US012590177B2

(12) United States Patent
Nakayama et al.

(10) Patent No.: US 12,590,177 B2
(45) **Date of Patent: *Mar. 31, 2026**

(54) COMPOUND, CURABLE RESIN COMPOSITION, CURED PRODUCT, OPTICAL MEMBER, AND LENS

(71) Applicant: FUJIFILM Corporation, Tokyo (JP)

(72) Inventors: Takafumi Nakayama, Ashigarakami-gun (JP); Kosuke Chiba, Ashigarakami-gun (JP); Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 535 days.

This patent is subject to a terminal disclaimer.

(21) Appl. No.: 18/166,278

(22) Filed: Feb. 8, 2023

(65) Prior Publication Data

US 2023/0183406 A1 Jun. 15, 2023

Related U.S. Application Data

(63) Continuation of application No. PCT/JP2021/029982, filed on Aug. 17, 2021.

(30) Foreign Application Priority Data

Aug. 21, 2020 (JP) ................................ 2020-140312

(51) Int. Cl.

| | |
|---|---|
| ***C08F 222/10*** | (2006.01) |
| ***C07C 69/616*** | (2006.01) |
| ***C07D 241/42*** | (2006.01) |
| ***G02B 1/04*** | (2006.01) |

(52) U.S. Cl.

CPC ...... *C08F 222/1025* (2020.02); *C07C 69/616* (2013.01); *C07D 241/42* (2013.01); *G02B 1/041* (2013.01); *C08F 2800/20* (2013.01)

(58) Field of Classification Search

None

See application file for complete search history.

(56) References Cited

U.S. PATENT DOCUMENTS

| | | |
|---|---|---|
| 2018/0305486 A1 | 10/2018 | Nakayama et al. |
| 2020/0181061 A1 | 6/2020 | Nakayama et al. |

FOREIGN PATENT DOCUMENTS

| | | | | |
|---|---|---|---|---|
| CN | 109957046 | A | | 7/2019 |
| CN | 111051363 | A | | 4/2020 |
| CN | 112876584 | A | | 6/2021 |
| JP | 2007-11005 | A | | 1/2007 |
| JP | 2007011005 | A | * | 1/2007 |
| JP | 2014-208804 | A | | 11/2014 |
| KR | 10-2018-0099343 | A | | 9/2018 |
| WO | 2013/090610 | A1 | | 6/2013 |
| WO | 2017/115649 | A1 | | 7/2017 |
| WO | 2019/120081 | A1 | | 6/2019 |

OTHER PUBLICATIONS

JP2007011005 English machine translation, prepared Jul. 31, 2025. (Year: 2025).*

International Preliminary Report on Patentability dated Feb. 16, 2023 with translation of Written Opinion of International Searching Authority in International Application No. PCT/JP2021/029982.

Written Opinion of International Searching Authority dated Oct. 5, 2021 in International Application No. PCT/JP2021/029982.

International Search Report dated Oct. 5, 2021 in International Application No. PCT/JP2021/029982.

Communication dated Mar. 27, 2024 issued by the State Intellectual Property Office of P.R. China in application No. 202180056739.2.

Notification of Reasons for Refusal dated May 9, 2023 from the Japanese Patent Office in corresponding application No. 2022-543944.

* cited by examiner

*Primary Examiner* — Christopher M Rodd

(74) *Attorney, Agent, or Firm* — Sughrue Mion, PLLC

(57) ABSTRACT

Provided are the following compound represented by General Formula (A) or (B), a curable resin composition including the compound, a cured product thereof, an optical member, and a lens:

General Formula (A)

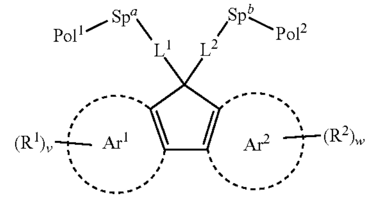

General Formula (B)

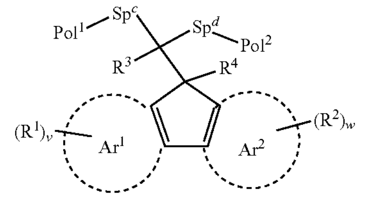

A ring $Ar^1$ and a ring $Ar^2$ represent an aromatic ring represented by a specific formula or a fused ring thereof, $R^1$ and $R^2$ represent a specific substituent, and v and w are a specific integer. $R^3$ and $R^4$ represent a hydrogen atom or a monovalent substituent, $L^1$ and $L^2$ represent an alkylene group having 1 to 6 carbon atoms, and $Sp^a$ to $Sp^d$ represent a single bond or a divalent linking group. $Pol^1$ and $Pol^2$ represent a hydrogen atom or a polymerizable group, in which at least one of $Pol^1$ or $Pol^2$ is a polymerizable group. Further, in the formulae, a structure represented by $(R^1)_v$—$Ar^1$/cyclopentadiene skeleton/$Ar^2$—$(R^2)_w$ is not line-symmetrical.

6 Claims, 1 Drawing Sheet

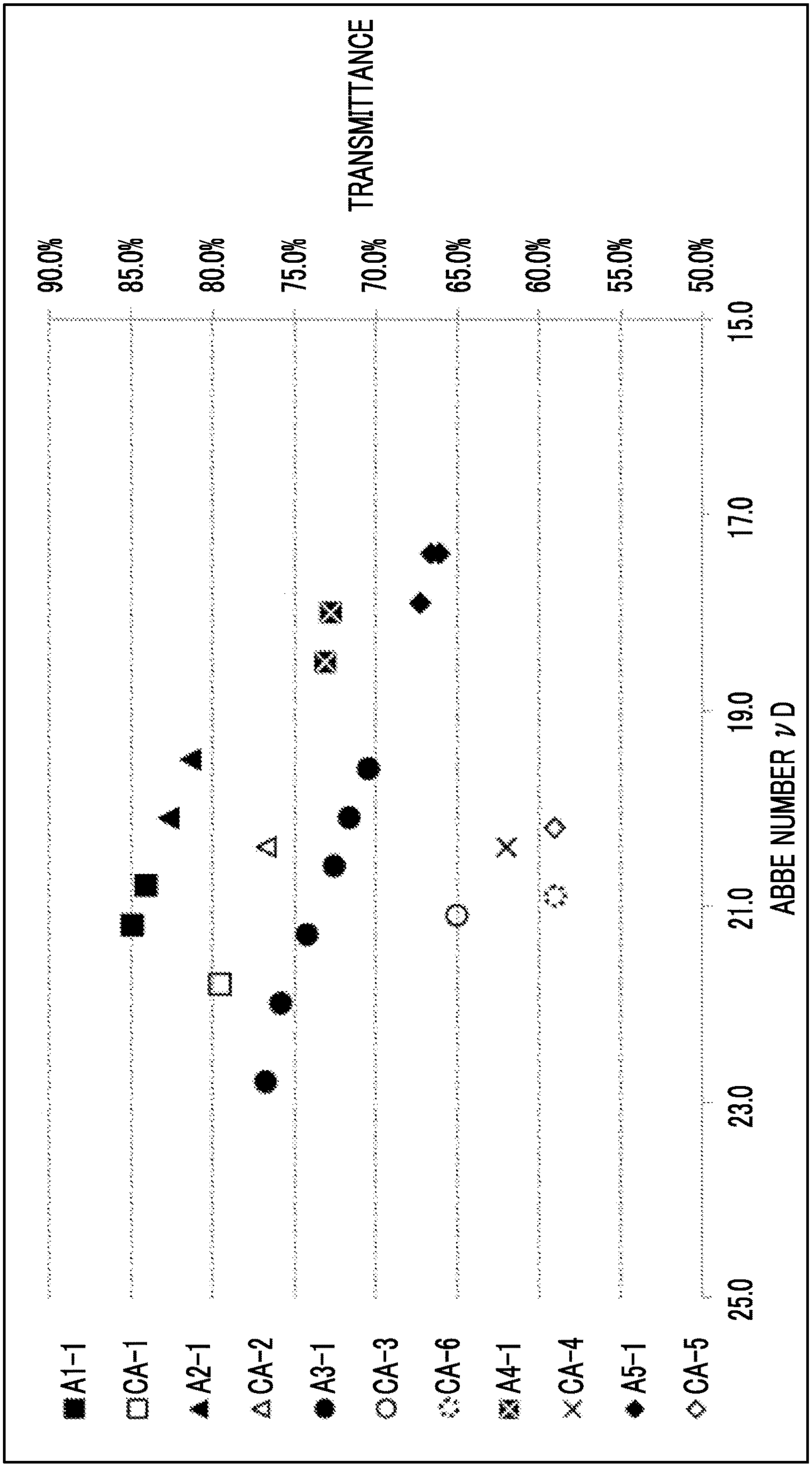
TRANSMITTANCE
90.0%
85.0%
80.0%
75.0%
70.0%
65.0%
60.0%
55.0%
50.0%
15.0
17.0
19.0
21.0
23.0
25.0
ABBE NUMBER ν D
A1-1
CA-1
A2-1
CA-2
A3-1
CA-3
CA-6
A4-1
CA-4
A5-1
CA-5

COMPOUND, CURABLE RESIN COMPOSITION, CURED PRODUCT, OPTICAL MEMBER, AND LENS

CROSS-REFERENCE TO RELATED APPLICATIONS

This application is a Continuation of PCT International Application No. PCT/JP2021/029982 filed on Aug. 17, 2021, which claims priority under 35 U.S.C. § 119 (a) to Japanese Patent Application No. 2020-140312 filed in Japan on Aug. 21, 2020. Each of the above applications is hereby expressly incorporated by reference, in its entirety, into the present application.

BACKGROUND OF THE INVENTION

1. Field of the Invention

The present invention relates to a compound, a curable resin composition, a cured product, an optical member, and a lens.

2. Description of the Related Art

In the related art, glass materials have been used for an optical member of an imaging module such as a camera, a video camera, a mobile phone with a camera, a video phone, or a door phone with a camera. The glass material has optical characteristics suitable for the optical member of the imaging module, can impart desired optical characteristics, and has excellent environmental resistance.

However, it is not easy to reduce a weight and size of the glass material, and workability and productivity are also deteriorated. On the other hand, since a resin cured product can be mass-produced and has excellent workability, with the miniaturization of the imaging module in the related art, the resin cured product has been used as an optical member to replace the glass material.

With the miniaturization of the imaging module, the optical member thereof is also required to be miniaturized. However, as the optical member is smaller, the problem of chromatic aberration arises. Accordingly, in an optical member formed of the resin cured product, examinations have been conducted regarding adjusting a small Abbe number using a monomer of a curable composition and additives, thereby correcting chromatic aberrations.

For example, JP2014-208804A discloses a curable resin composition containing a fused ring-containing compound (monomer) in which a (meth)acryloyl group is bonded through a phenylene group to a fluorene-type skeleton having four or more fused rings, and discloses that a cured product exhibiting a low Abbe number (νD) is obtained by using this resin compound.

In addition, WO2017/115649A discloses a compound (monomer) in which a (meth)acryloyl group is bonded through a phenylene group to a fluorene-type skeleton including a nitrogen atom as a ring-constituting atom, and discloses that a cured product having a low Abbe number (νD) and a high partial dispersion ratio (θg, F value) is obtained by using a curable composition containing this compound.

SUMMARY OF THE INVENTION

As a result of studies by the present inventors, in a case where a content of the compound disclosed in JP2014-208804A or WO2017/115649A in the curable composition is increased in order to obtain a cured product having a lower Abbe number, the Abbe number can be decreased. However, in this case, it has been found that there is a problem that transmittance of the cured product also decreases.

An object of the present invention is to provide a compound with which a cured product that a sufficiently low Abbe number and an excellent transmittance are achieved can be obtained. Another object of the present invention is to provide a curable resin composition containing the compound, a cured product obtained from this curable resin composition, and an optical member and a lens including this cured product.

As a result of intensive studies to solve the above-described problems, the present inventors have found that, by using, as a raw material of a cured product, a compound obtained by introducing a polymerizable group into an asymmetric fluorene-type skeleton through an alkylene group, excellent transmittance can be achieved while sufficiently suppressing the Abbe number of the obtained cured product.

That is, the above-described objects of the present invention have been achieved by the following methods.

<1>

A compound represented by General Formula (A) or (B)

General Formula (A)

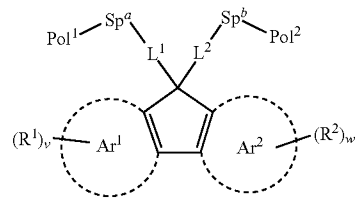

General Formula (B)

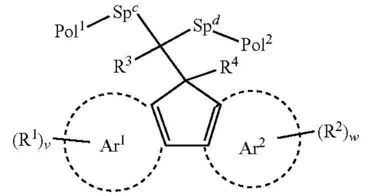

in the formulae, $R^3$ and $R^4$ represent a hydrogen atom or a monovalent substituent, $L^1$ and $L^2$ represent an alkylene group having 1 to 6 carbon atoms, and $Sp^a$ to $Sp^d$ represent a single bond or a divalent linking group, $Pol^1$ and $Pol^2$ represent a hydrogen atom or a polymerizable group, where at least one of $Pol^1$ or $Pol^2$ is a polymerizable group, a ring $Ar^1$ represents an aromatic ring represented by Formula (AR1) or a fused ring including the aromatic ring as a ring constituting the fused ring, and a ring $Ar^2$ represents an aromatic ring represented by Formula (AR2) or a fused ring including the aromatic ring as a ring constituting the fused ring, $R^1$ represents a substituent adopted by a ring-constituting atom of the ring $Ar^1$, and $R^2$ represents a substituent adopted by a ring-constituting atom of the ring $Ar^2$, v is an integer of 0 or more, and a maximum number of v is a maximum number of substituents which are able to be adopted by the ring-constituting atom of the ring $Ar^1$, and w is an integer of 0 or more, and a maximum number of w is a maximum number of substituents which are able to be adopted by the ring-constituting atom of the ring $Ar^2$, Formula (AR1)

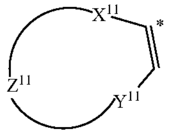

Formula (AR2)

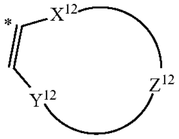

in the formulae, $X^{11}$, $Y^{11}$, $X^{12}$, and $Y^{12}$ represent an oxygen atom, a sulfur atom, a nitrogen atom, or a carbon atom, $Z^{11}$ represents an atomic group which forms a 5- to 7-membered aromatic ring together with —$X^{12}$—C═C—$Y^{11}$— and is composed of atoms selected from an oxygen atom, a sulfur atom, a nitrogen atom, and a carbon atom, $Z^{12}$ represents an atomic group which forms a 5- to 7-membered aromatic ring together with —$X^{12}$—C═C—$Y^{12}$— and is composed of atoms selected from an oxygen atom, a sulfur atom, a nitrogen atom, and a carbon atom, and

* corresponds to a double bond of a cyclopentadiene ring in General Formula (A) or (B), where in General Formulae (A) and (B), a structure represented by $(R^1)_v$—$Ar^1$/cyclopentadiene skeleton/$Ar^2$—$(R^2)_w$ is not line-symmetrical, in which "/" represents that two rings described on left and right sides of the structure are fused.

<2>

The compound according to <1>, in which the compound is represented by General Formula (A).

<3>

The compound according to <1> or <2>, in which $Pol^1$ and $Pol^2$ are an acryloyloxy group or a methacryloyloxy group.

<4>

The compound according to any one of <1> to <3>, in which the compound is represented by General Formula (A1), General Formula (A1)

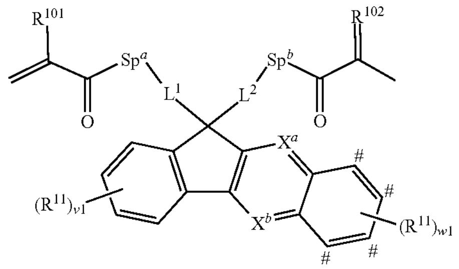

in the formula, $X^a$ and $X^b$ represent a nitrogen atom or CH, CH at a position of # may be substituted by a nitrogen atom, $R^{11}$ and $R^{21}$ represent a substituent, v1 and w1 are an integer of 0 to 4, and $R^{101}$ and $R^{102}$ represent a hydrogen atom or a methyl group, and $L^1$, $L^2$, $Sp^a$, and $Sp^b$ have the same meanings as $L^1$, $L^2$, $Sp^a$, and $Sp^b$ in General Formula (A), respectively.

<5>

A curable resin composition comprising:

the compound according to any one of <1> to <4>.

<6>

The curable resin composition according to <5>, in which a content of the compound according to any one of <1> to <4> in the curable resin composition is 50% by mass or more.

<7>

A cured product of the curable resin composition according to <5> or <6>.

<8>

An optical member comprising:

the cured product according to <7>.

<9>

A lens comprising:

the cured product according to <7>.

In the present invention, in a case of a plurality of substituents, linking groups, or the like (hereinafter, referred to as a substituent or the like) represented by a specific reference or formula, or in a case of simultaneously defining a plurality of the substituent and the like, unless otherwise specified, the substituent and the like may be the same or different from each other (regardless of the presence or absence of an expression "each independently", the substituent and the like may be the same or different from each other). The same applies to the definition of the number of substituents and the like. In a case where a plurality of substituents and the like are near (particularly, adjacent to each other), unless otherwise specified, the substituents and the like may be linked to each other to form a ring. In addition, unless otherwise specified, a ring, for example, an alicyclic ring, an aromatic ring, or a heterocyclic ring may be further fused to form a fused ring.

In the present invention, unless otherwise specified, with regard to a double bond, in a case where E-form and Z-form are present in the molecule, the double bond may be any one of these forms, or may be a mixture thereof.

In addition, in the present invention, unless otherwise specified, in a case where a compound has one or two or more asymmetric carbons, for such stereochemistry of asymmetric carbons, either an (R)-form or an (S)-form can be independently taken. As a result, the compound may be a mixture of optical isomers or stereoisomers such as diastereoisomers, or may be racemic.

In addition, in the present invention, the expression of the compound means that a compound having a partially changed structure is included within a range which does not impair the effects of the present invention. Further, a compound which is not specifically described as substituted or unsubstituted may have an optional substituent within a range which does not impair the effects of the present invention.

In the present invention, with regard to a substituent (the same applies to a linking group and a ring) in which whether it is substituted or unsubstituted is not specified, within a range not impairing the desired effect, it means that the group may have an optional substituent. For example, "alkyl group" means to include both an unsubstituted alkyl group and a substituted alkyl group.

In the present invention, in a case where the number of carbon atoms in a certain group is specified, the number of carbon atoms means the number of carbon atoms in the entire group, unless otherwise specified in the present invention or the present specification. That is, in a case of a form in which the group has a substituent, it means the total number of carbon atoms including the substituent. For example, the number of carbon atoms in the "linear alkylene group" which can be adopted as $L^1$ and $L^2$ means the number of carbon atoms in a state in which a substituent is not included, as described later.

In the present invention, a numerical range represented by using "to" means a range including numerical values described before and after "to" as a lower limit value and an upper limit value.

In the curable resin composition according to the aspect of the present invention, each component may be used alone or in combination of two or more thereof. The same applies to the cured product, the optical member, and the lens obtained from the curable resin composition according to the aspect of the present invention.

In a description of a content of each component in the curable resin composition according to the aspect of the present invention, a solid content in the curable resin composition according to the aspect of the present invention means, in addition to the compound represented by General Formula (A) or (B), components remaining in the cured product obtained from the curable resin composition according to the aspect of the present invention. Usually, a remainder after removing a solvent is the "solid content".

In the present invention, an Abbe number means an Abbe number νD calculated by a method described later.

In the present invention, "(meth)acrylate" represents either one or both of acrylate and methacrylate, and "(meth) acryloyl" represents either one or both of acryloyl and methacryloyl. The monomer in the present invention is distinguished from an oligomer and a polymer, and refers to a compound having a weight-average molecular weight of 1000 or less.

In the present invention, the term aliphatic hydrocarbon group represents a group obtained by removing one optional hydrogen atom from a linear or branched alkane, a linear or branched alkene, or a linear or branched alkyne. In the present invention, the aliphatic hydrocarbon group is preferably an alkyl group obtained by removing one optional hydrogen atom from a linear or branched alkane. Examples of the alkyl group include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, a 2-ethylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

In addition, in the present invention, the aliphatic hydrocarbon group (unsubstituted) is preferably an alkyl group having 1 to 12 carbon atoms, and particularly preferably a methyl group or an ethyl group.

In the present invention, the term alkyl group indicates a linear or branched alkyl group. Examples of the alkyl group include the above-described examples. The same applies to an alkyl group in a group (an alkoxy group, an alkoxycarbonyl group, an acyl group, an acyloxy group, a carbamoyl group, an acylamino group, an amino group, and the like) including the alkyl group.

In addition, in the present invention, examples of a linear alkylene group include a group obtained by removing one hydrogen atom bonded to a terminal carbon atom from a linear alkyl group among the above-described alkyl groups.

In the present invention, the term alicyclic hydrocarbon ring means a saturated hydrocarbon ring (cycloalkane). Examples of the alicyclic hydrocarbon ring include cyclopropane, cyclobutane, cyclopentane, cyclohexane, cycloheptane, cyclooctane, cyclononane, and cyclodecane.

In the present invention, the term unsaturated hydrocarbon ring means a hydrocarbon ring having a carbon-carbon unsaturated double bond, which is not an aromatic ring. Examples of the unsaturated hydrocarbon ring include indene, indane, and fluorene.

In the present invention, the term alicyclic hydrocarbon group means a cycloalkyl group obtained by removing one optional hydrogen atom from a cycloalkane. Examples of the alicyclic hydrocarbon group include a cyclopropyl group, a cyclobutyl group, a cyclopentyl group, a cyclohexyl group, a cycloheptyl group, a cyclooctyl group, a cyclononyl group, and a cyclodecyl group, and a cycloalkyl group having 3 to 12 carbon atoms is preferable.

In the present invention, a cycloalkylene group refers to a divalent group obtained by removing two optional hydrogen atoms from a cycloalkane. Examples of the cycloalkylene group include a cyclohexylene group.

In the present invention, the term aromatic ring means either one or both of an aromatic hydrocarbon ring and an aromatic heterocyclic ring.

In the present invention, the term aromatic hydrocarbon ring means an aromatic ring in which a ring is formed only by carbon atoms. The aromatic hydrocarbon ring may be a monocyclic ring or a fused ring. An aromatic hydrocarbon ring having 6 to 14 carbon atoms is preferable. Examples of aromatic hydrocarbon rings include a benzene ring, a naphthylene ring, an anthracene ring, a phenanthrene ring, and the like. In the present invention, in a case where the aromatic hydrocarbon ring is bonded to another ring, it is sufficient that the aromatic hydrocarbon ring may be substituted on another ring as a monovalent or divalent aromatic hydrocarbon ring group.

In the present invention, in a case where a monovalent group is referred to as an aromatic hydrocarbon ring group, it indicates a monovalent group obtained by removing any one hydrogen atom from an aromatic hydrocarbon ring. As the monovalent aromatic hydrocarbon ring group is preferably an aromatic hydrocarbon ring group having 6 to 14 carbon atoms, and examples of the monovalent aromatic hydrocarbon group include a phenyl group, a biphenyl group, an 1-naphthyl group, a 2-naphthyl group, an 1-anthracenyl group, a 2-anthracenyl group, a 3-anthracenyl group, a 4-anthracenyl group, a 9-anthracenyl group, an 1-phenanthryl group, a 2-phenanthryl group, a 3-phenanthryl group, a 4-phenanthryl group, and a 9-phenanthryl group. Among these, a phenyl group is preferable.

In the present invention, in a case where a divalent group is referred to as an aromatic hydrocarbon ring group, it indicates a divalent group obtained by removing any one hydrogen atom from the above-described monovalent aromatic hydrocarbon ring group. Examples of divalent aromatic hydrocarbon ring groups include a phenylene group, a naphthylene group, a phenanthrylene group, and the like, and a phenylene group is preferable and a 1,4-phenylene group is more preferable.

In the present invention, an aromatic heterocyclic ring means an aromatic ring in which a ring is formed by a carbon atom and a heteroatom. Examples of the heteroatom include an oxygen atom, a nitrogen atom, and a sulfur atom. The aromatic heterocyclic ring may be a monocyclic ring or a fused ring, and the number of atoms constituting the ring is preferably 5 to 20 and more preferably 5 to 14. The number of heteroatoms in the atoms constituting the ring is not particularly limited, but is preferably 1 to 3 and more preferably 1 or 2. Examples of the aromatic heterocyclic ring include a furan ring, a thiophene ring, a pyrrole ring, an imidazole ring, an isothiazole ring, an isoxazole ring, a pyridine ring, a pyrazine ring, a quinoline ring, a benzofuran ring, a benzothiazole ring, a benzoxazole ring, and examples of nitrogen-containing fused aromatic ring described later. In the present invention, in a case where the aromatic heterocyclic ring is bonded to another ring, it is sufficient that the aromatic heterocyclic ring may be substituted on another ring as a monovalent or divalent aromatic heterocyclic group.

In the present invention, in a case where a monovalent group is referred to as an aromatic heterocyclic group, it indicates a monovalent group obtained by removing any one hydrogen atom from an aromatic heterocyclic ring. Examples of the monovalent aromatic heterocyclic group include a furyl group, a thienyl group, a pyrrolyl group, an imidazolyl group, an isothiazolyl group, an isooxazolyl group, a pyridyl group, a pyrazinyl group, a quinolyl group, a benzofuranyl group (preferably, a 2-benzofuranyl group), a benzothiazolyl group (preferably, a 2-benzothiazolyl group), and a benzoxazolyl group (preferably, a 2-benzoxazolyl group). Among these, a furyl group, a thienyl group, a benzofuranyl group, a benzothiazolyl group, or a benzoxazolyl group is preferable, and a 2-furyl group or a 2-thienyl group is more preferable.

In the present invention, the term divalent aromatic heterocyclic group refers to a divalent group obtained by removing two optional hydrogen atoms from the aromatic heterocyclic ring, and examples thereof include a divalent group obtained by removing one optional hydrogen atom from the above-described (monovalent) aromatic heterocyclic group.

In the present invention, examples of a halogen atom include a fluorine atom, a chlorine atom, a bromine atom, and an iodine atom.

In the present invention, the structure represented by the following notation indicates an isopropylene structure. This isopropylene structure may be any of two structural isomers in which a methyl group is bonded to one of carbon atoms constituting an ethylene group, and these structural isomers may be mixed.

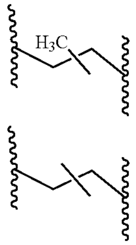

or

With the compound according to the aspect of the present invention, a cured product that a sufficiently low Abbe number and an excellent transmittance are achieved can be obtained. In addition, with the curable resin composition according to the aspect of the present invention, a cured product obtained by curing the curable resin composition can achieve a sufficiently low Abbe number and an excellent transmittance. The cured product, the optical member, and the lens according to the aspect of the present invention can exhibit excellent transmittance with a sufficiently low Abbe number.

BRIEF DESCRIPTION OF THE DRAWINGS

The FIGURE is a graph showing a relationship between an Abbe number νD and a transmittance in cured products produced in Examples and Comparative Examples.

DESCRIPTION OF THE PREFERRED EMBODIMENTS

The present invention will be described in detail. The description of configuration requirements described below may be based on representative embodiments, specific examples, and the like, but the present invention is not limited to those embodiments except as specified in the present invention.

A compound according to an embodiment of the present invention is a compound represented by General Formula (A) or (B) described later. Details of a structure of the compound will be described later, but first, a technical significance of the compound according to the embodiment of the present invention will be described.

Compared to the compound in which the (meth)acryloyl group is bonded through a phenylene group to a specific fluorene-type skeleton as disclosed in JP2014-208804A or WO2017/115649A, the compound according to the embodiment of the present invention can achieve both a low Abbe number and a high transmittance in a cured product at a high level. The reason for this is not clear, but it is considered to be as follows.

As described above, the compound disclosed in JP2014-208804A or WO2017/115649A is a compound in which a (meth)acryloyl group is bonded through a phenylene group to a fluorene-type skeleton that four or more rings are fused or a fluorene-type skeleton including a nitrogen atom as a ring-constituting atom. According to JP2014-208804A or WO2017/115649A, it is considered that the Abbe number of the cured product of the curable resin composition including the compound disclosed in JP2014-208804A or WO2017/115649A is lower than an Abbe number (approximately 28) exhibited by a cured product of a curable resin composition including a polymerizable compound having a 9,9-bisarylfluorene skeleton in the related art. However, in order to obtain a cured product having a lower Abbe number, it is necessary to increase a content of the above-described compound disclosed in JP2014-208804A or WO2017/115649A in the cured product. However, the increase in content leads to a decrease in transmittance of the cured product, which makes it impossible to satisfy requirements as an optical member.

As a result of intensive studies to obtain a cured product exhibiting a lower Abbe number and a high transmittance, the present inventors have found that, by adopting a structure of the compound represented by General Formula (A) or (B), in which an alkylene group is bonded to a specific fluorene-type skeleton, and using this compound as a raw material compound for a cured product, it is possible to realize a cured product which achieves both optical characteristics, such as a low Abbe number and a high transmittance, which are thought to be in a so-called trade-off relationship with each other in the related art, at a high level.

This is because the compound disclosed in JP2014-208804A or WO2017/115649A, in which the phenylene group is bonded to a specific fluorene-type skeleton, has a maximal absorption wavelength in an ultraviolet region on a long wavelength side, whereas the compound represented by General Formula (A) or (B) according to the embodiment of the present invention, in which the alkylene group is bonded to a specific fluorene-type skeleton, has a maximal absorption wavelength in a short wavelength side. Therefore, it is considered that the transmittance of the cured product is improved.

[Compound]

The compound according to the embodiment of the present invention is represented by General Formula (A) or (B).

General Formula (A)

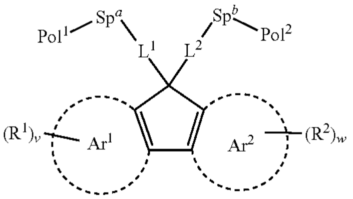

General Formula (B)

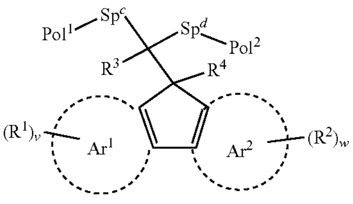

In the formulae, $R^3$ and $R^4$ represent a hydrogen atom or a monovalent substituent, $L^L$ and $L^2$ represent an alkylene group having 1 to 6 carbon atoms, and $Sp^a$ to $Sp^d$ represent a single bond or a divalent linking group.

$Pol^1$ and $Pol^2$ represent a hydrogen atom or a polymerizable group. However, at least one of $Pol^1$ or $Pol^2$ is a polymerizable group.

A ring $Ar^1$ represents an aromatic ring represented by Formula (AR1) described later or a fused ring including the aromatic ring as a ring constituting the fused ring, and a ring $Ar^2$ represents an aromatic ring represented by Formula (AR2) described later or a fused ring including the aromatic ring as a ring constituting the fused ring.

$R^1$ represents a substituent adopted by a ring-constituting atom of the ring $Ar^1$, and $R^2$ represents a substituent adopted by a ring-constituting atom of the ring $Ar^2$.

v is an integer of 0 or more, and a maximum number of v is a maximum number of substituents which can be adopted by the ring-constituting atom of the ring $Ar^1$.

w is an integer of 0 or more, and a maximum number of w is a maximum number of substituents which can be adopted by the ring-constituting atom of the ring $Ar^2$.

However, in General Formulae (A) and (B), a structure represented by $(R^1)_v$—$Ar^1$/cyclopentadiene skeleton/$Ar^2$—$(R^2)_w$ is not line-symmetrical. "/" represents that two rings described on left and right sides of the structure are fused.

A compound represented by any of General Formula (A) or General Formula (B) is classified into the compound represented by General Formula (A).

As described above, one of characteristic structures of the compound represented by General Formula (A) or (B) according to the embodiment of the present invention is that a fused-ring structure represented by $(R^1)_v$—$Ar^1$/cyclopentadiene skeleton/$Ar^2$—$(R^2)_w$ does not adopt a line-symmetrical structure. Here, "/" represents that the cyclopentadiene skeleton is fused with the ring $Ar^1$ and the ring $Ar^2$. In addition, the "cyclopentadiene skeleton" means a ring structure of cyclopentadiene, excluding a substituent.

That is, the above-described definition of the compound represented by General Formula (A) or (B) means that the ring $Ar^1$ having v pieces of the substituents $R^1$ and the ring $Ar^2$ having w pieces of the substituents $R^2$, which are located on both sides of the 5-membered ring (cyclopentadiene structure), are different in at least one of the following points.

(i) mother nucleus structures of the ring $Ar^1$ and the ring $Ar^2$ (ii) substitution positions of the substituents $R^1$ and the substituents $R^2$ with respect to the mother nucleus, and (iii) structures of the substituent $R^1$ and the substituent $R^2$ Among these, it is preferable that at least the point (i) is different between the rings.

Hereinafter, the substituent, the linking group, and the reference numeral in General Formula (A) or (B) will be described in detail.

(1) $L^1$ and $L^2$ $L^1$ and $L^2$ represent an alkylene group having 1 to 6 carbon atoms, and an alkylene group having 1 to 4 carbon atoms is preferable and an alkylene group having 2 or 3 carbon atoms is more preferable. The alkylene group may be linear or branched.

The number of linking atoms constituting the shortest molecular chain which links $Sp^a$ or $Sp^b$ with the 5-membered ring in which the ring $Ar^1$ and the ring $Ar^2$ are fused is preferably 1 to 6, more preferably 1 to 4, and still more preferably 2 or 3.

$L^1$ and $L^2$ are determined such that the number of carbon atoms in the alkylene group constituting $L^1$ and $L^2$ is maximized. That is, in General Formula (A), among the divalent linking groups which can be adopted as the following $Sp^a$ and $Sp^b$, the portion bonded to $L^1$ or $L^2$ is not an alkylene group.

Examples of the substituent which may be included in the alkylene group of $L^1$ and $L^2$ described above include a cycloalkyl group, an alkoxy group, an acyl group, an acyloxy group, an alkoxycarbonyl group, a carbamoyl group, an acylamino group, an amino group, a halogen atom, a nitro group, a cyano group, and a group represented by -Sp-Pol.

Sp represents a single bond or a divalent linking group, and the description of $Sp^a$ below can be adopted. Pol is a polymerizable group, and the description of the polymerizable group in $Pol^1$ later can be adopted.

As the substituent which may be included in the alkylene group of $L^1$ and $L^2$ described above, an alkoxy group, an alkoxycarbonyl group, or a group represented by -Sp-Pol is preferable, —COO-alkylene-Pol is more preferable, and —COO-alkylene-$OCOCH{=}CH_2$ or —COO— alkylene-$OCOC(CH_3){=}CH_2$ is still more preferable.

In a case where the alkylene group of $L^1$ and $L^2$ described above has a substituent, the number of substituents is not particularly limited, but for example, the alkylene group may have 1 to 4 substituents, preferably has 1 or 2 substituents and more preferably has 1 substituent.

It is preferable that the alkylene group of $L^1$ and $L^2$ described above does not have a substituent.

(2) $Sp^a$ and $Sp^b$ $Sp^a$ and $Sp^b$ represent a single bond or a divalent linking group.

Examples of the divalent linking group which can be adopted as $Sp^a$ or $Sp^b$ include a divalent linking group formed by bonding one or two or more groups selected from a linear alkylene group, a cycloalkylene group, —O—, —S—, >C(═O), and >$NR^{201}$.

The $R^{201}$ represents a hydrogen atom or an alkyl group having 1 to 3 carbon atoms.

However, among the divalent linking groups which can be adopted as the following $Sp^a$ and $Sp^b$, the portion bonded to $L^1$ or $L^2$ is not a linear alkylene group or a cycloalkylene group.

The number of carbon atoms in the above-described linear alkylene group is preferably 1 to 8, more preferably 1 to 6, still more preferably 1 to 4, and particularly preferably 1 or 2.

The number of carbon atoms in the above-described cycloalkylene group is preferably 3 to 6.

The carbon atoms in the above-described "linear alkylene group" mean the carbon number in a state without a substituent. In a case where the "linear alkylene group" has a substituent, an alkyl group can also be adopted as the substituent. In this case, the alkylene group is a branched alkylene group as a whole, but the number of linking atoms in the portion corresponding to the shortest molecular chain linking $L^1$ and $Pol^1$ or $L^2$ and $Pol^2$ in $Sp^a$ and $Sp^b$ corresponds to the number of carbon atoms in the above-described "linear alkylene group".

The carbon atoms in the above-described "cycloalkylene group" mean the carbon number in a state without a substituent.

Examples of the substituent which may be included in the linear alkylene group or the cycloalkylene group of $Sp^a$ and $Sp^b$ described above include an alkyl group, a cycloalkyl group, an alkoxy group, an acyl group, an acyloxy group, an alkoxycarbonyl group, a carbamoyl group, an acylamino group, an amino group, a halogen atom, a nitro group, and a cyano group, and an alkyl group is preferable, an alkyl group having 1 to 3 carbon atoms is more preferable, and a methyl group is still more preferable.

The number of substituents is not particularly limited, and for example, may be 1 to 4.

The number of the linear alkylene group, cycloalkylene group, —O—, —S—, >C(═O), and >$NR^{201}$ constituting $Sp^a$ and $Sp^b$ which are a divalent linking group is preferably 1 to 5 and more preferably 1 to 3.

In $Sp^a$ and $Sp^b$ which are a divalent linking group, examples of the group formed by linking two or more of —O—, —S—, >C(═O), and >$NR^{201}$ include —C(═O)O—, —$NR^{201}$C(═O)—, —SC(═O)—, —OC(═O)O—, and —$NR^{201}$C(═O)O—, and —C(═O)O—, —$NR^{201}$C(═O)—, or —SC(═O)— is preferable and —C(═O)O— is more preferable.

It is sufficient that the above-described group formed by linking two or more of —O—, —S—, >C(═O), and >$NR^{201}$ constitutes $Sp^a$ and $Sp^b$ which are a divalent linking group alone or together with at least one of the linear alkylene group or the cycloalkylene group, and it is preferable that the above-described group constitutes $Sp^a$ and $Sp^b$ which are a divalent linking group together with at least one of the linear alkylene group or the cycloalkylene group.

The —C(═O)O—, —$NR^{201}$C(═O)—, —$NR^{201}$C(═O)O—, or —SC(═O)— may be disposed in a form such that either the left or right bonding site is located on the $L^1$ side or the $L^2$ side.

In $Sp^a$ and $Sp^b$, from the viewpoint of increasing a ratio of a fused structural portion consisting of the cyclopentadiene skeleton, $Ar^1$, and $Ar^2$ in the compound, in a case where $Sp^a$ or $Sp^b$ is a divalent linking group, the number of linking atoms constituting the shortest molecular chain linking $L^1$ and $Pol^1$ or $L^2$ and $Pol^2$ is preferably 1 to 10, more preferably 1 to 8, still more preferably 1 to 6, and particularly preferably 1 to 4. In a case where $Sp^a$ or $Sp^b$ is a single bond, the number of linking atoms constituting the shortest molecular chain linking $L^1$ and $Pol^1$ or $L^2$ and $Pol^2$ is 0, and this aspect is also preferable from the above-described viewpoint. For example, in an exemplary compound (A1-1) described later, the number of linking atoms constituting the shortest molecular chain linking $L^1$ and $Pol^1$ or $L^2$ and $Pol^2$ is 4.

As the divalent linking group which can be adopted as $Sp^a$ or $Sp^b$, a divalent linking group formed by bonding one or two or more groups selected from a linear alkylene group, —O—, and >C(═O) is preferable, >C(═O), —O-linear alkylene-, or —C(═O)O-linear alkylene- is more preferable, and —C(═O)O-linear alkylene- is still more preferable.

As $Sp^a$ and $Sp^b$, a single bond or a divalent linking group formed by bonding one or two or more groups selected from a linear alkylene group, —O—, and >C(═O) is preferable, a single bond, >C(═O), —O-linear alkylene-, or —C(═O)O-linear alkylene- is more preferable, and —C(═O)O-linear alkylene- is still more preferable.

$Sp^a$ and $Sp^b$ may be the same or different from each other, but it is preferable that $Sp^a$ and $Sp^b$ are the same.

(3) $Sp^c$ and $Sp^d$ $Sp^c$ and $Sp^d$ represent a single bond or a divalent linking group.

Examples of the divalent linking group which can be adopted as $Sp^c$ or $Sp^d$ include a divalent linking group formed by bonding one or two or more groups selected from a linear alkylene group, a cycloalkylene group, —O—, —S—, >C(═O), and >$NR^{201}$.

The $R^{201}$ represents a hydrogen atom or an alkyl group having 1 to 3 carbon atoms.

The number of carbon atoms in the above-described linear alkylene group is preferably 1 to 8, more preferably 1 to 6, still more preferably 1 to 4, and particularly preferably 1 or 2.

The number of carbon atoms in the above-described cycloalkylene group is preferably 3 to 6.

The carbon atoms in the above-described "linear alkylene group" mean the carbon number in a state without a substituent. In a case where the "linear alkylene group" has a substituent, an alkyl group can also be adopted as the substituent. In this case, the alkylene group is a branched alkylene group as a whole, but the number of linking atoms in the portion corresponding to the shortest molecular chain linking $CR^3$ and $Pol^1$ or $CR^3$ and $Pol^2$ in $Sp^c$ and $Sp^d$ corresponds to the number of carbon atoms in the above-described "linear alkylene group".

The carbon atoms in the above-described "cycloalkylene group" mean the carbon number in a state without a substituent.

Examples of the substituent which may be included in the linear alkylene group or the cycloalkylene group of $Sp^c$ and $Sp^d$ described above include an alkyl group, a cycloalkyl group, an alkoxy group, an acyl group, an acyloxy group, an alkoxycarbonyl group, a carbamoyl group, an acylamino group, an amino group, a halogen atom, a nitro group, and a cyano group, and an alkyl group is preferable, an alkyl group having 1 to 3 carbon atoms is more preferable, and a methyl group is still more preferable.

The number of substituents is not particularly limited, and for example, may be 1 to 4.

The number of the linear alkylene group, cycloalkylene group, —O—, —S—, >C(═O), and >$NR^{201}$ constituting $Sp^c$ and $Sp^d$ which are a divalent linking group is preferably 1 to 5 and more preferably 1 to 3.

In $Sp^c$ and $Sp^d$ which are a divalent linking group, examples of the group formed by linking two or more of —O—, —S—, >C(=O), and >$NR^{201}$ include —C(=O)O—, —$NR^{201}$C(=O)—, —SC(=O)—, —OC(=O)O—, and —$NR^{201}$C(=O)O—, and —C(=O)O—, —$NR^{201}$C(=O)—, or —SC(=O)— is preferable and —C(=O)O— is more preferable.

It is sufficient that the above-described group formed by linking two or more of —O—, —S—, >C(=O), and >$NR^{201}$ constitutes $Sp^c$ and $Sp^d$ which are a divalent linking group alone or together with at least one of the linear alkylene group or the cycloalkylene group, and it is preferable that the above-described group constitutes $Sp^c$ and $Sp^d$ which are a divalent linking group together with at least one of the linear alkylene group or the cycloalkylene group.

The —C(=O)O—, —$NR^{201}$C(=O)—, —$NR^{201}$C(=O)O—, or —SC(=O)— may be disposed in a form such that either the left or right bonding site is located on the $CR^3$ side.

In $Sp^c$ and $Sp^d$, from the viewpoint of increasing a ratio of a fused structural portion consisting of the cyclopentadiene skeleton, $Ar^1$, and $Ar^2$ in the compound, in a case where $Sp^c$ or $Sp^d$ is a divalent linking group, the number of linking atoms constituting the shortest molecular chain linking $CR^3$ and $Pol^1$ or $CR^3$ and $Pol^2$ is preferably 1 to 10, more preferably 1 to 8, still more preferably 1 to 6, particularly preferably 1 to 5, and most preferably 1 to 4. In a case where $Sp^c$ or $Sp^d$ is a single bond, the number of linking atoms constituting the shortest molecular chain linking $CR^3$ and $Pol^1$ or $CR^3$ and $Pol^2$ is 0, and this aspect is also preferable from the above-described viewpoint. For example, in an exemplary compound (A1-7) described later, the number of linking atoms constituting the shortest molecular chain linking $CR^3$ and $Pol^1$ or $CR^3$ and $Pol^2$ is 4 for one and 5 for the other.

As the divalent linking group which can be adopted as $Sp^c$ or $Sp^d$, a divalent linking group formed by bonding one or two or more groups selected from a linear alkylene group, —O—, and >C(=O) is preferable, >C(=O), —O-alkylene-, or —C(=O)O-alkylene- is more preferable, and —C(=O)O-alkylene- is still more preferable.

As $Sp^c$ and $Sp^d$, a single bond or a divalent linking group formed by bonding one or two or more groups selected from a linear alkylene group, —O—, and >C(=O) is preferable, a single bond, >C(=O), —O-alkylene-, -alkylene-O-alkylene-, —C(=O)O-alkylene-, or -alkylene-C(=O)O-alkylene- is more preferable, and —C(=O)O-alkylene- or -alkylene-C(=O)O-alkylene- is still more preferable.

$Sp^c$ and $Sp^d$ may be the same or different from each other, but it is preferable that $Sp^a$ and $Sp^b$ are different from each other.

As $Sp^c$ and $Sp^d$, it is preferable that one of $Sp^c$ or $Sp^d$ is -alkylene-C(=O)O-alkylene- and the other is —C(=O)O-alkylene-.

(4) $R^3$ and $R^4$ $R^3$ and $R^4$ represent a hydrogen atom or a monovalent substituent.

Examples of the monovalent substituent which may be adopted as $R^3$ and $R^4$ include an alkyl group, a cycloalkyl group, an alkoxy group, an acyl group, an acyloxy group, an alkoxycarbonyl group, a carbamoyl group, an acylamino group, an amino group, a halogen atom, a nitro group, and a cyano group, and an alkyl group is preferable.

The number of carbon atoms in the alkyl group which can be adopted as $R^3$ and $R^4$ is preferably 1 to 6, more preferably 1 to 4, and still more preferably 1 or 2.

$R^3$ and $R^4$ are preferably a hydrogen atom.

(5) $Pol^1$ and $Pol^2$ $Pol^1$ and $Pol^2$ represent a hydrogen atom or a polymerizable group. However, at least one of $Pol^1$ or $Pol^2$ is a polymerizable group.

The polymerizable group which may be adopted as $Pol^1$ and $Pol^2$ may be a group including any of a vinylidene structure, an oxirane structure, or an oxetane structure. From the viewpoint of convenience in synthesizing the compound represented by General Formula (A) or (B), the polymerizable group is preferably a group in which the linking part to $Sp^a$ to $Sp^d$ is an oxygen atom and which includes any of a vinylidene structure, an oxirane structure, or an oxetane structure, and examples thereof include polymerizable groups represented by any of Formulae (Pol-1) to (Pol-6).

Formula (Pol-1)

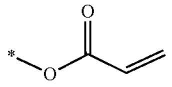

Formula (Pol-2)

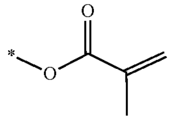

Formula (Pol-3)

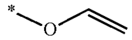

Formula (Pol-4)

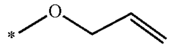

Formula (Pol-5)

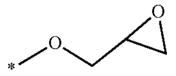

Formula (Pol-6)

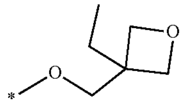

*represents a bonding position.

Among these, an acryloyloxy group represented by Formula (Pol-1) or a methacryloyloxy group represented by Formula (Pol-2) is preferable, and a methacryloyloxy group represented by Formula (Pol-2) is more preferable.

It is preferable that any one of $Pol^1$ or $Pol^2$ is a (meth)acryloyloxy group, and it is more preferable that the both are (meth)acryloyloxy groups.

$Pol^1$ and $Pol^2$ may be the same or different from each other, but it is preferable that $Pol^1$ and $Pol^2$ are the same.

(6) Ring $Ar^1$ and ring $Ar^2$

The ring $Ar^1$ represents an aromatic ring represented by Formula (AR1) or a fused ring including the aromatic ring as a ring constituting the fused ring, and the ring $Ar^2$ represents an aromatic ring represented by Formula (AR2) or a fused ring including the aromatic ring as a ring constituting the fused ring.

In a case where the ring $Ar^1$ and the ring $Ar^2$ are fused rings, the number of ring members in each ring constituting the fused ring is preferably 5 to 7, more preferably 5 or 6, and still more preferably 6.

In addition, in a case where the ring $Ar^1$ and the ring $Ar^2$ are fused rings, the number of rings constituting the fused ring is preferably 2 or 3, and more preferably 2. It is preferable that one of the ring $Ar^1$ or the ring $Ar^2$ is a monocyclic ring represented by Formula (AR1) or (AR2)

and the other is a fused ring. The number of rings constituting this fused ring is preferably 2.

Among ring-constituting atoms constituting the fused ring, as a ring-constituting atom other than the ring represented by Formula (AR1) or (AR2), a carbon atom, an oxygen atom, a sulfur atom, or a nitrogen atom is preferable, a carbon atom or a nitrogen atom is more preferable, and a carbon atom is still more preferable.

As the ring other than the ring represented by Formula (AR1) or (AR2), which constitutes the fused ring, for example, a benzene ring or a pyridine ring is preferable.

Formula (AR1)

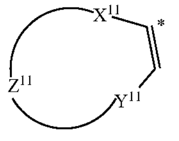

Formula (AR2)

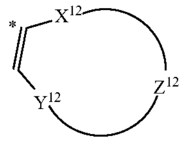

In the formulae, $X^{11}$, $Y^{11}$, $X^{12}$, and $Y^{12}$ represent an oxygen atom, a sulfur atom, a nitrogen atom, or a carbon atom.

$Z^{11}$ represents an atomic group which forms a 5- to 7-membered aromatic ring together with $—X^{11}—C═C—Y^{11}—$ and is composed of atoms selected from an oxygen atom, a sulfur atom, a nitrogen atom, and a carbon atom.

$Z^{12}$ represents an atomic group which forms a 5- to 7-membered aromatic ring together with $—X^{12}—C═C—Y^{12}—$ and is composed of atoms selected from an oxygen atom, a sulfur atom, a nitrogen atom, and a carbon atom.

* corresponds to a double bond of a cyclopentadiene ring in General Formula (A) or (B). That is, the cyclopentadiene ring is fused with the ring $Ar^1$ and the ring $Ar^2$ while sharing a side indicated by *.

($X^{11}$, $Y^{11}$, $X^{12}$, and $Y^{12}$)

The $X^{11}$, $Y^{11}$, $X^{12}$, and $Y^{12}$ represent an oxygen atom, a sulfur atom, a nitrogen atom, or a carbon atom, and a nitrogen atom or a carbon atom is preferable.

Among these, in a case where the ring $Ar^1$ described below is a monocyclic ring, it is preferable that both $X^{11}$ and $Y^{11}$ are carbon atoms, and in a case where the ring $Ar^1$ described below is a fused ring, it is preferable that both $X^{11}$ and $Y^{11}$ are nitrogen atoms or carbon atoms.

Similarly, in a case where the ring $Ar^2$ described below is a monocyclic ring, it is preferable that both $X^{12}$ and $Y^{12}$ are carbon atoms, and in a case where the ring $Ar^2$ described below is a fused ring, it is preferable that both $X^{12}$ and $Y^{12}$ are nitrogen atoms or carbon atoms.

($Z^{11}$ and $Z^{12}$)

$Z^{11}$ is an atomic group which forms a 5- to 7-membered aromatic ring together with $—X^{11}—C═C—Y^{11}—$ and is preferably an atomic group forming a 5- or 6-membered aromatic ring and more preferably an atomic group forming a 6-membered aromatic ring.

$Z^{12}$ is an atomic group which forms a 5- to 7-membered aromatic ring together with $—X^{12}—C═C—Y^{12}—$ and is preferably an atomic group forming a 5- or 6-membered aromatic ring and more preferably an atomic group forming a 6-membered aromatic ring.

$Z^{11}$ and $Z^{12}$ are an atomic group composed of atoms selected from an oxygen atom, a sulfur atom, a nitrogen atom, and a carbon atom. $Z^{11}$ and $Z^{12}$ are an atomic group composed of atoms selected from an oxygen atom, a sulfur atom, a nitrogen atom, and a carbon atom, and are preferably an atomic group including at least carbon atom and more preferably an atomic group consisting of carbon atoms.

(7) $R^1$ and $R^2$ $R^1$ represents a substituent adopted by a ring-constituting atom of the ring $Ar^1$, and $R^2$ represents a substituent adopted by a ring-constituting atom of the ring $Ar^2$. Each of $R^1$ and $R^2$ is a substituent which may be included in a nitrogen atom or a carbon atom respectively by NH or CH in a case of unsubstituted, among the ring-constituting atoms in the ring $Ar^1$ or the ring $Ar^2$.

The substituent which may be adopted as $R^1$ and $R^2$ is not particularly limited, and examples thereof include a halogen atom, an alkyl group, an acyl group, a hydroxy group, an alkoxy group, an aromatic hydrocarbon ring group, and a cyano group.

The substitution position of $R^1$ in the ring $Ar^1$ and the substitution position of $R^2$ in the ring $Ar^2$ are not particularly limited.

The number of carbon atoms in the alkyl group which can be adopted as $R^1$ and $R^2$ is preferably 1 to 5, more preferably 1 to 3, and still more preferably 1.

The number of carbon atoms in the alkoxy group which can be adopted as $R^1$ and $R^2$ is preferably 1 to 5, more preferably 1 to 3, and still more preferably 1.

The number of carbon atoms in the aromatic hydrocarbon ring group which can be adopted as $R^1$ and $R^2$ is preferably 6 to 14 and more preferably 6 to 10.

As the halogen atom which can be adopted as $R^1$ and $R^2$, a fluorine atom, a chlorine atom, or a bromine atom is preferable, and a chlorine atom is more preferable.

$R^1$ and $R^2$ are preferably a halogen atom, an alkyl group, an alkoxy group, an aromatic hydrocarbon ring group, or a cyano group, more preferably a halogen atom, an alkyl group having 1 to 5 carbon atoms, or an alkoxy group having 1 to 5 carbon atoms, and still more preferably a halogen atom, a methyl group, or a methoxy group.

(8) v and w v is an integer of 0 or more, and the maximum number of v is the maximum number of substituents which can be adopted by the ring-constituting atom of the ring $Ar^1$.

w is an integer of 0 or more, and the maximum number of w is the maximum number of substituents which can be adopted by the ring-constituting atom of the ring $Ar^2$.

v and w are preferably an integer of 0 to 4 and more preferably an integer of 0 to 2.

The total of v and w is preferably an integer of 0 to 4 and more preferably an integer of 0 to 2.

The compound according to the embodiment of the present invention is preferably the compound represented by General Formula (A) described above, and more preferably a compound represented by General Formula (A1).

General Formula (A1)

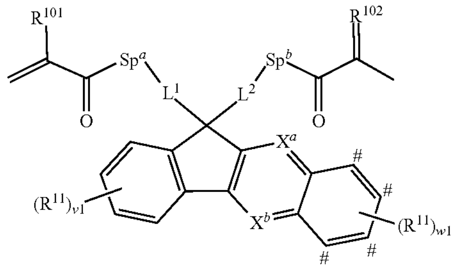

In the formula, $X^a$ and $X^b$ represent a nitrogen atom or CH, CH at a position of # may be substituted by a nitrogen atom.

$R^{11}$ and $R^{21}$ represent a substituent, v1 and w1 are an integer of 0 to 4, and $R^{101}$ and $R^{102}$ represent a hydrogen atom or a methyl group.

$L^1$, $L^2$, $Sp^a$, and $Sp^b$ have the same meanings as $L^1$, $L^2$, $Sp^a$, and $Sp^b$ in General Formula (A), respectively.

v1 and w1 are preferably an integer of 0 to 2.

As the substituent which can be adopted as $R^{11}$ and $R^{21}$, the description of the substituent which can be adopted as $R^1$ and $R^2$ described above can be applied.

$R^{21}$ is a substituent that may be included in the carbon atom in CH which may be adopted by $X^a$ and $X^b$ and the carbon atom in CH at the position of #.

In a case where $R^{11}$ or $R^{21}$ is provided, the substitution position of $R^{11}$ or $R^{21}$ is not particularly limited, but it is preferable to have $R^{11}$ or $R^{21}$ at a position represented by the following structure.

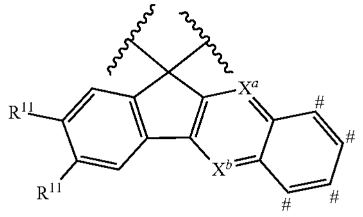

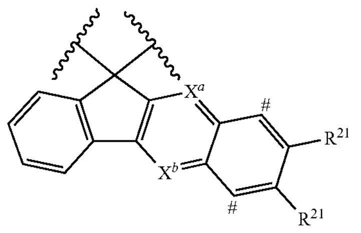

It is preferable that both $X^a$ and $X^b$ are CH or nitrogen atoms.

In addition, it is preferable that none of CH's at the position of # is substituted by the nitrogen atom.

That is, the compound represented by General Formula (A1) is preferably a compound represented by General Formula (A1-1) or (A1-2).

General Formula (A1-1)

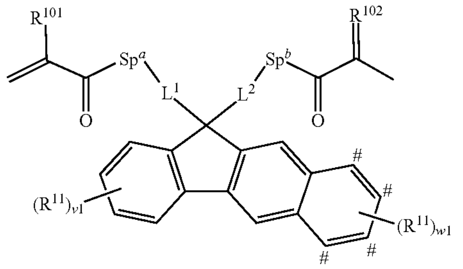

General Formula (A1-2)

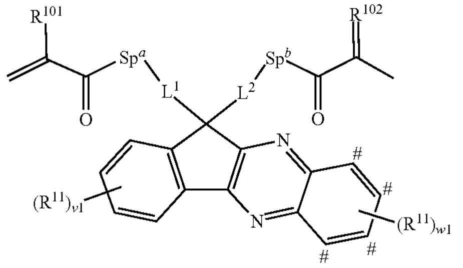

In the above formulae, $R^1$, $R^{21}$, $R^{101}$, $R^{102}$, $L^1$, $L^2$, $Sp^a$, $Sp^b$, v1, and w1 have the same meanings as $R^{11}$, $R^{21}$, $R^{101}$, $R^{102}$, $L^1$, $L^2$, $Sp^a$, $Sp^b$, v1, and w1 in General Formula (A1) described above.

The compound according to the embodiment of the present invention is preferably a non-liquid crystalline compound. That is, from the viewpoint of using as a lens material, it is preferable that the $Sp^a$ to $Sp^d$ are linking groups having no ring structure.

Hereinafter, preferred specific examples of the compound represented by General Formula (A) or (B) are listed, but the present invention is not limited to these compounds. In the following structural formulae, Me represents a methyl group.

(A1-1)

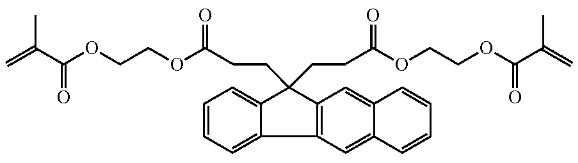

(A1-2)

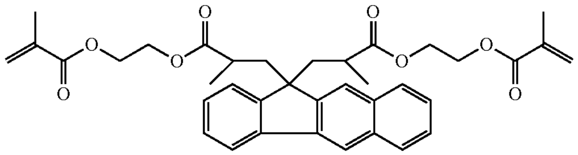

(A1-3)

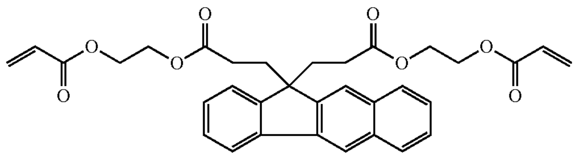

-continued
(A1-4)
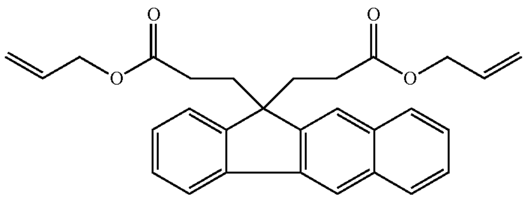
(A1-5)
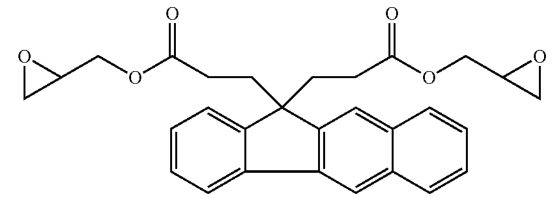
(A1-6)
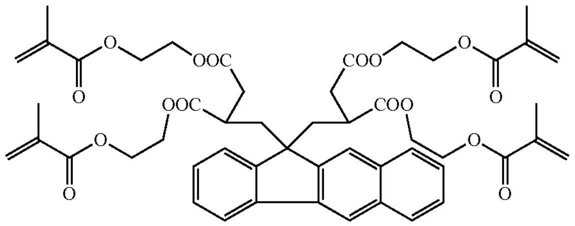
(A1-7)
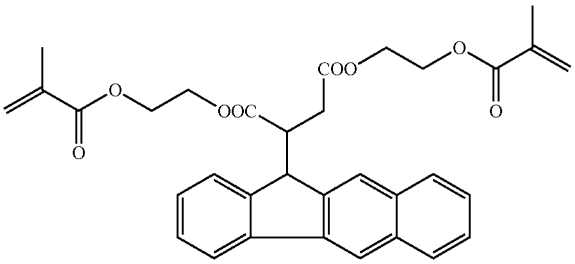
(A1-8)
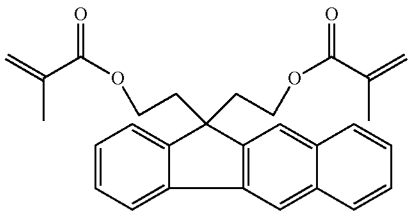
(A1-9)
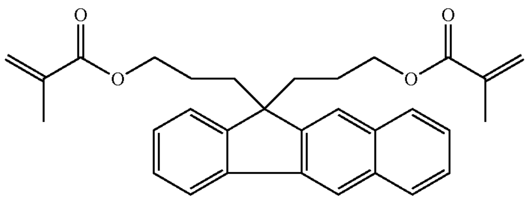
-continued
(A1-10)
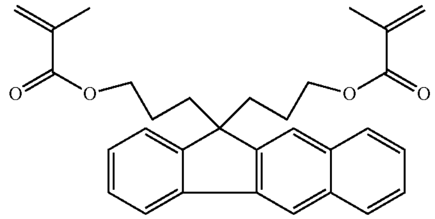
(A1-11)
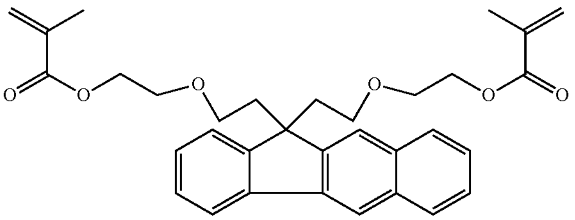
(A2-1)
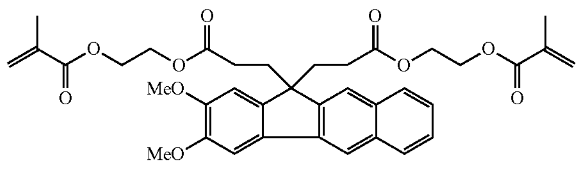
(A2-2)
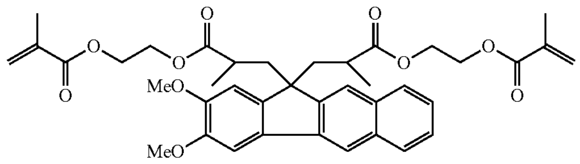
(A2-3)
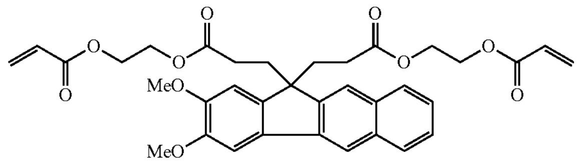
(A2-4)
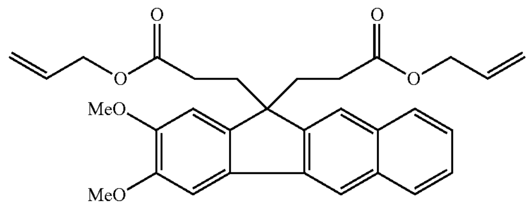
(A2-5)
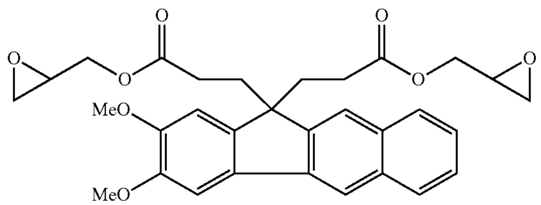

-continued
(A2-6)
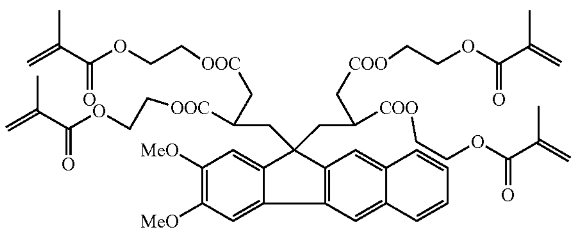
(A2-7)
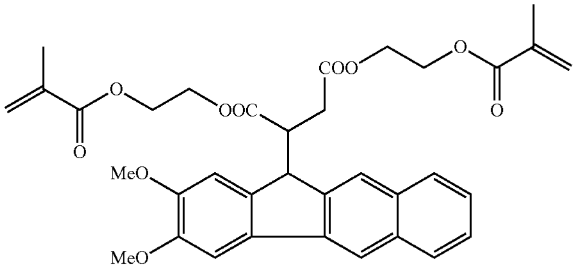
(A2-8)
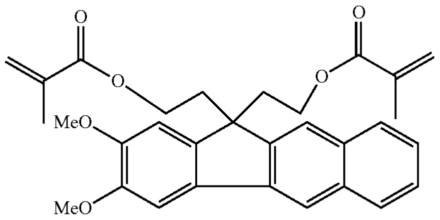
(A2-9)
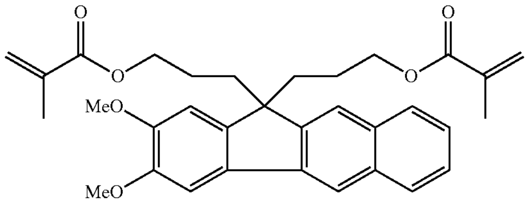
(A2-10)
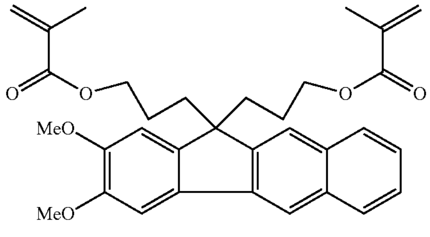
(A2-11)
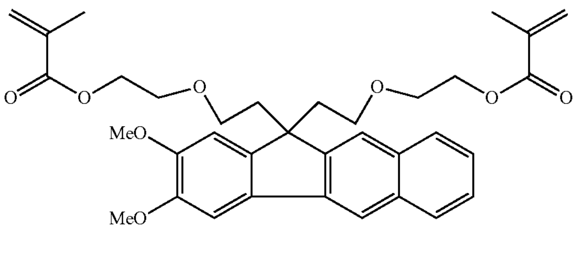
-continued
(A3-1)
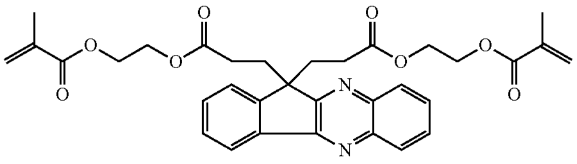
(A3-2)
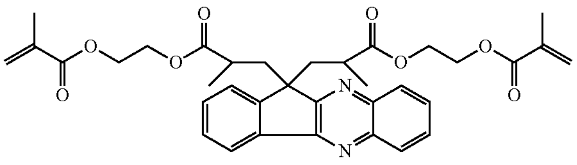
(A3-3)
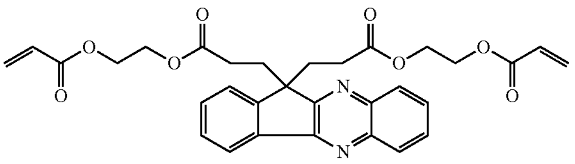
(A3-4)
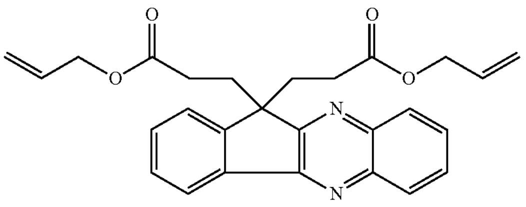
(A3-5)
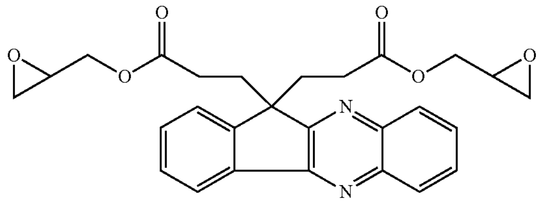
(A3-6)
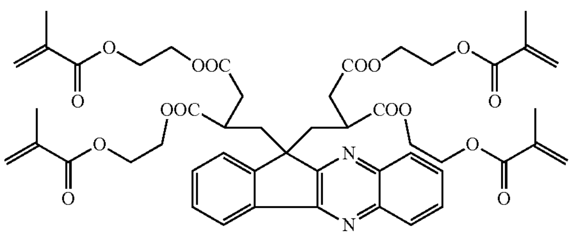
(A3-7)
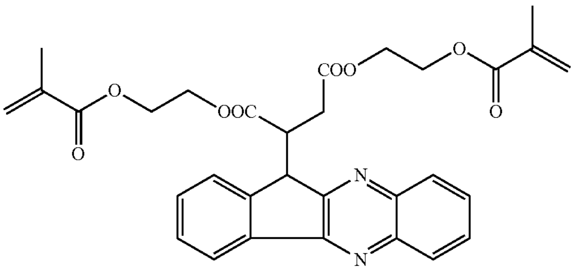

-continued
(A3-8)
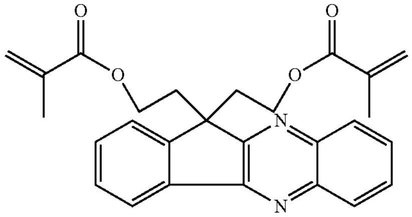
(A3-9)
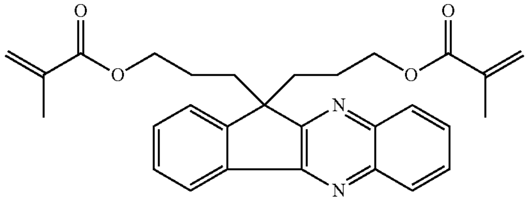
(A3-10)
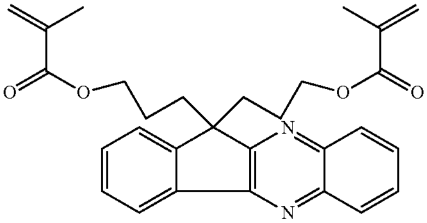
(A3-11)
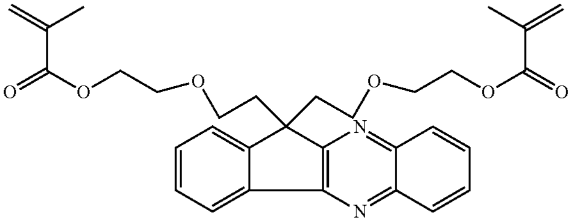
(A4-1)
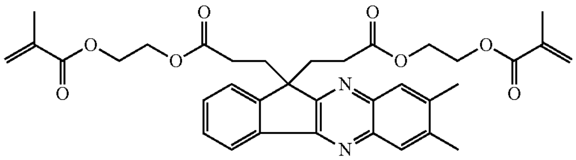
(A4-2)
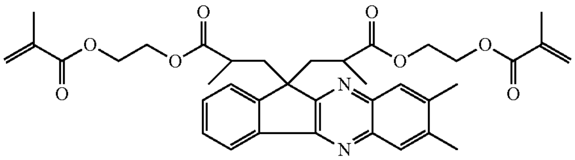
(A4-3)
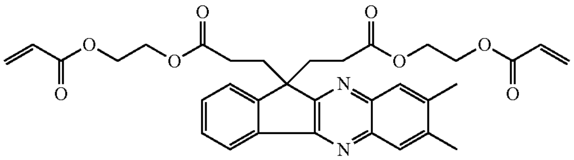
-continued
(A4-4)
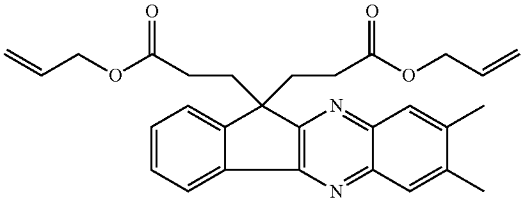
(A4-5)
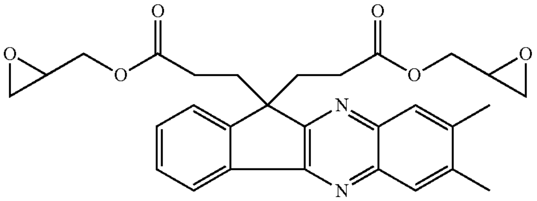
(A4-6)
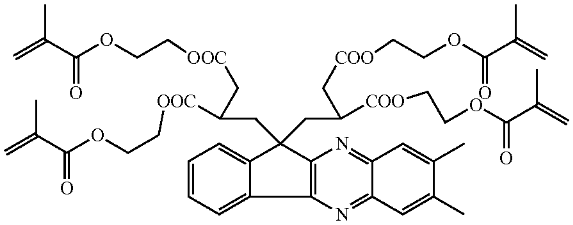
(A4-7)
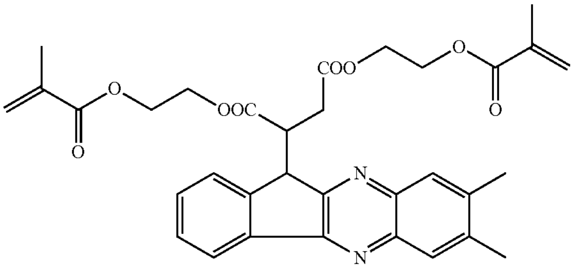
(A4-8)
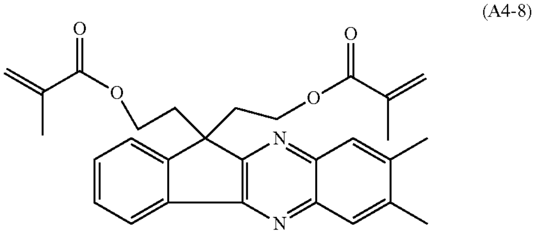
(A4-9)
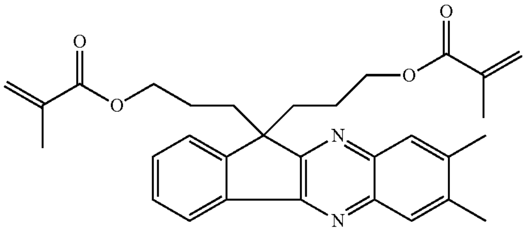

-continued
(A4-10)
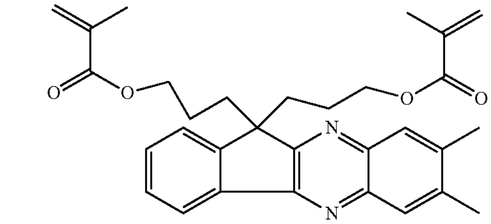
(A4-11)
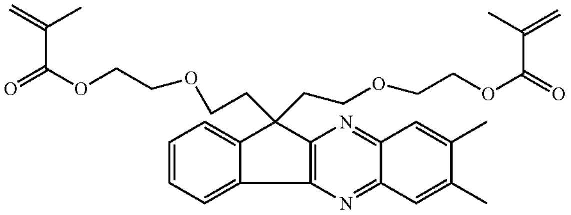
(A5-1)
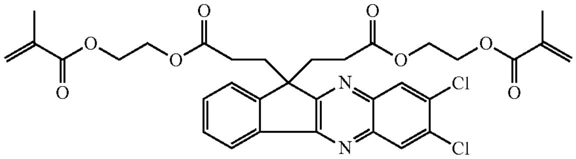
(A5-2)
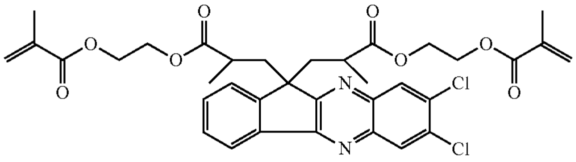
(A5-3)
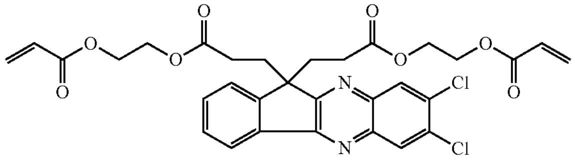
(A5-4)
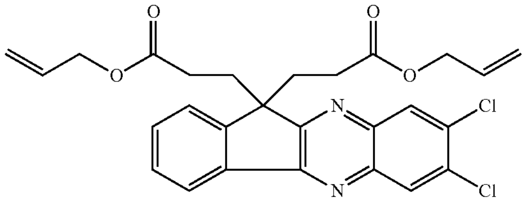
(A5-5)
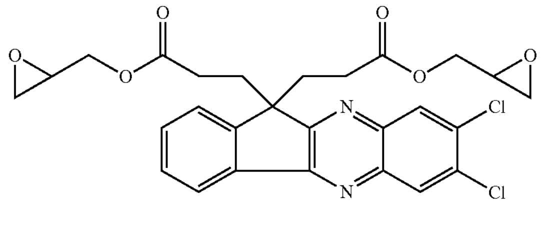
-continued
(A5-6)
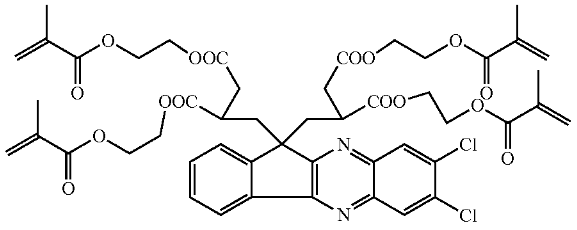
(A5-7)
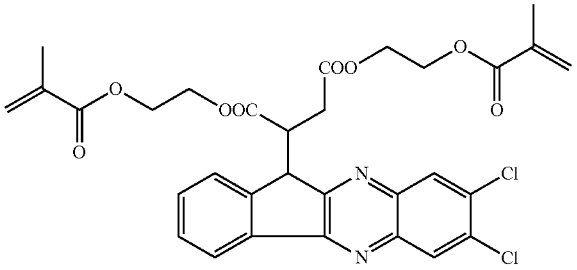
(A5-8)
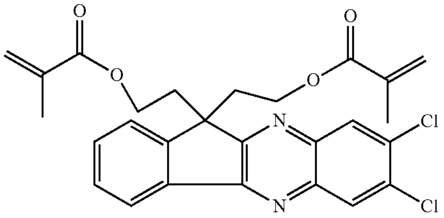
(A5-9)
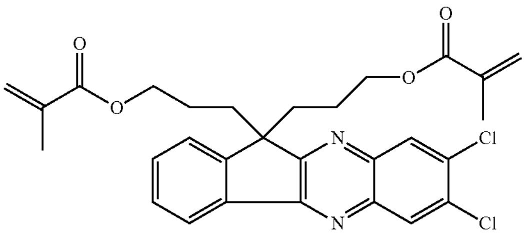
(A5-10)
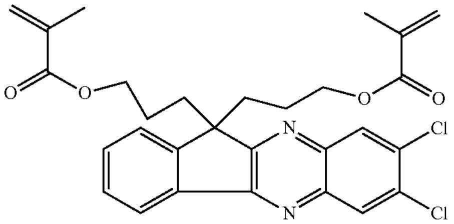
(A5-11)
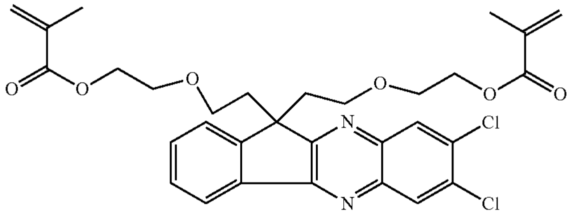

-continued
(A6-1)
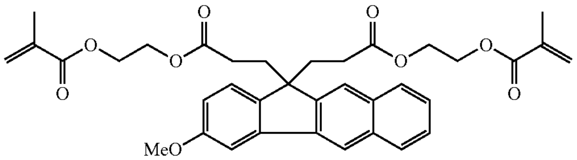
(A7-1)
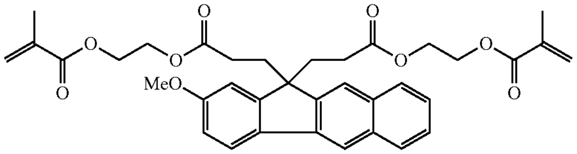
(A8-1)
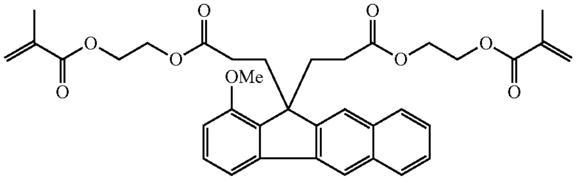
(A9-1)
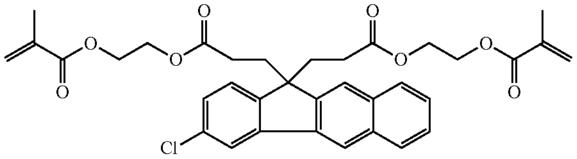
(A10-1)
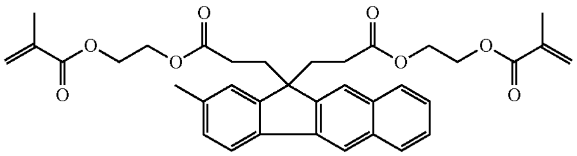
(A11-1)
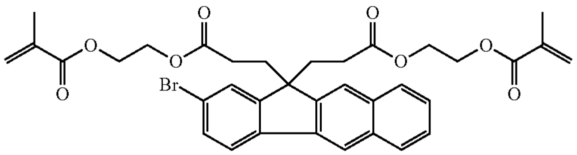
(A12-1)
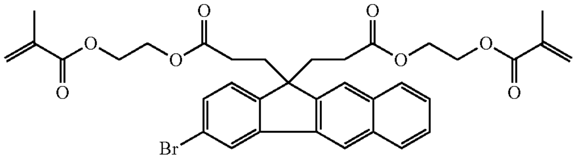
(A13-1)
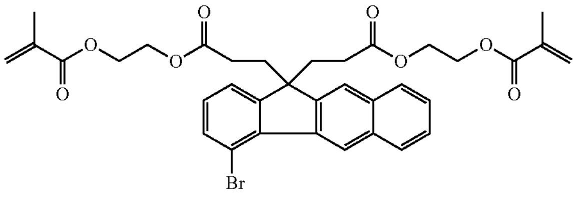
-continued
(A14-1)
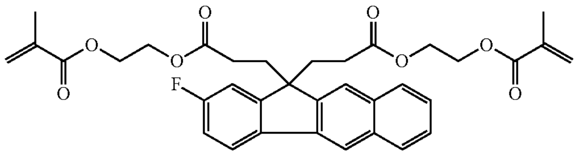
(A15-1)
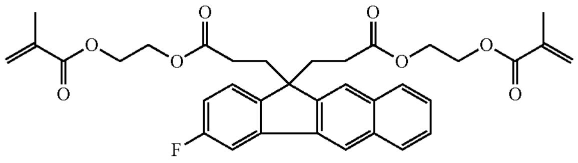
(A16-1)
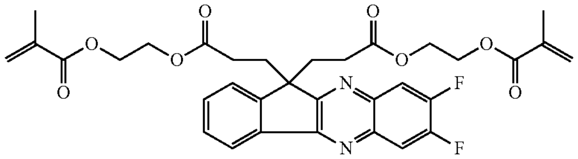
(A17-1)
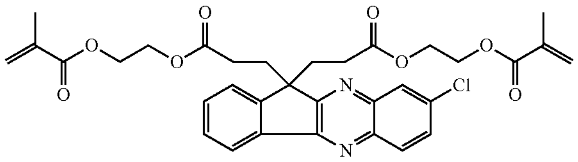
(A18-1)
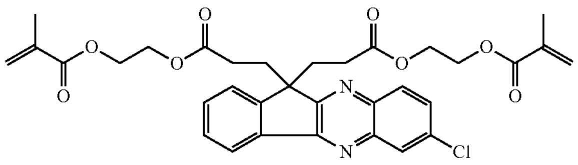
(A19-1)
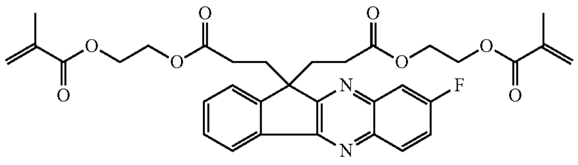
(A20-1)
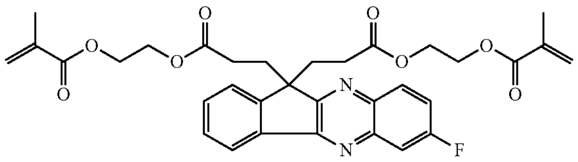
(A21-1)
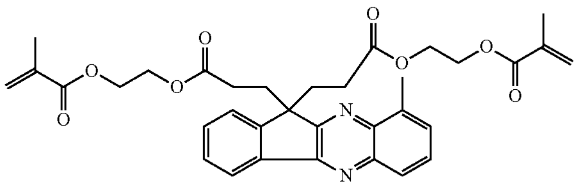

-continued (A22-1)

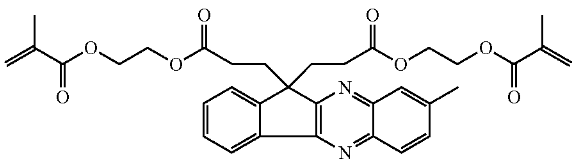

(A23-1)

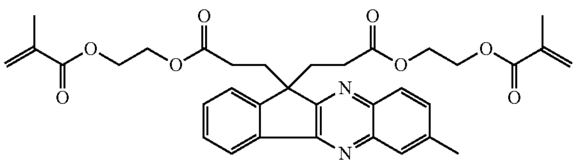

(A24-1)

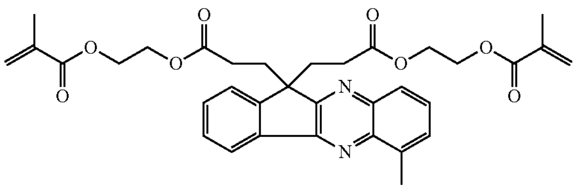

(A25-1)

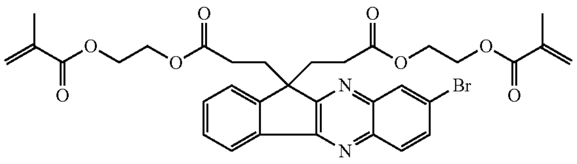

(A26-1)

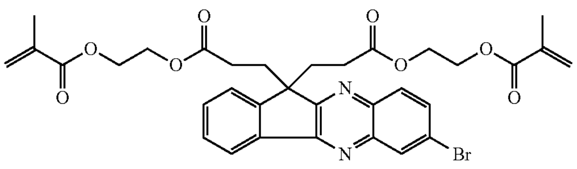

(A27-1)

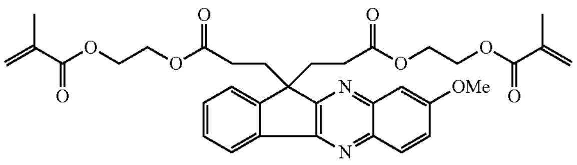

(A28-1)

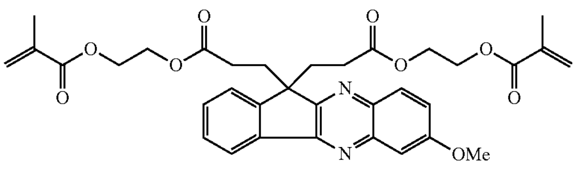

(A29-1)

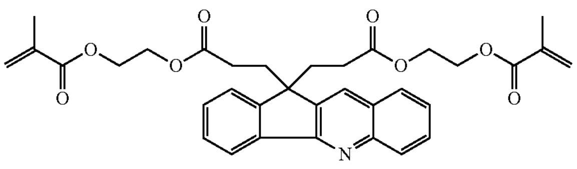

-continued (A30-1)

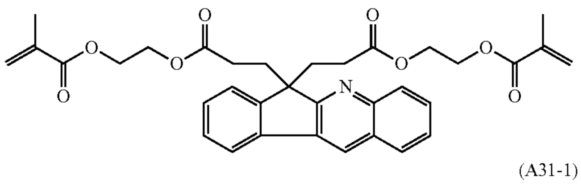

(A31-1)

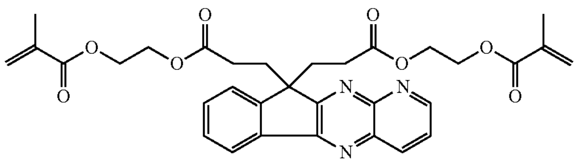

(A32-1)

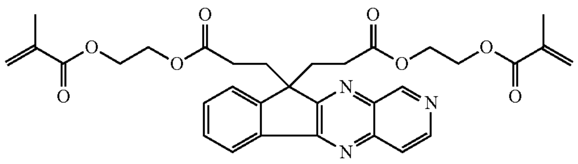

(A33-1)

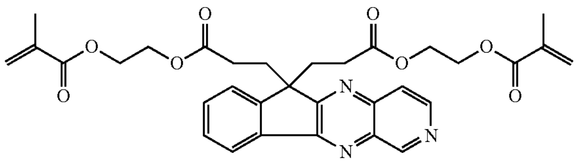

(A34-1)

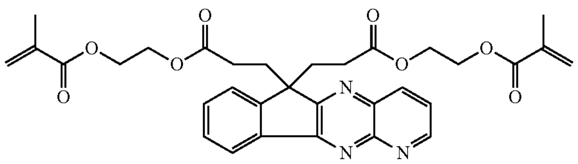

A molecular weight of the compound represented by General Formula (A) or (B) is preferably 400 to 1000, more preferably 500 to 900, and particularly preferably 550 to 800.

A method for obtaining the compound represented by General Formula (A) or (B) is not particularly limited, and the compound represented by General Formula (A) or (B) may be obtained commercially or may be obtained by synthesis. In a case of being obtained by synthesis, a method for producing (method for synthesizing) the compound represented by General Formula (A) or (B) is not particularly limited, and the compound represented by General Formula (A) or (B) can be synthesized by a conventional method or with reference to a method described in Examples. For example, the synthesis can be performed with reference to the synthesis method described in JP2002-179611A, the synthesis method described in [0078] and [0162] of WO2014/050738A (JP5682094B), and the like.

For example, a dicarboxylic acid product is obtained by subjecting a compound represented by General Formula (S) to an addition reaction with an ethylenically unsaturated carboxylic acid in the presence of a base or by subjecting the compound represented by General Formula (S) to an addition reaction with an ethylenically unsaturated carboxylic acid ester or an ethylenically unsaturated dicarboxylic acid anhydride in the presence of a base, followed by hydrolysis. Alternatively, a dicarboxylic acid product which is a precursor of the compound represented by General Formula (A) is obtained by subjecting the compound represented by General Formula (S) to a substitution reaction with an alkylcarboxylic acid ester having a leaving group (for example, a halogen atom) at the ω-position in the presence of a base, and then hydrolyzing an ester group (for example, a dicarboxylic acid ester product having two carboxymethyl groups can be obtained by a substitution reaction with butyl bromoacetate). The compound represented by General Formula (A) or (B) can be obtained by conducting an ester reaction to introduce a group corresponding to $Pol^1$ and $Pol^2$ in General Formula (A) or (B) to the obtained dicarboxylic acid product. In a case where one equivalent of an ethylenically unsaturated carboxylic acid, an ethylenically unsaturated carboxylic acid ester, or an ethylenically unsaturated dicarboxylic acid anhydride is reacted with (introduced into) the compound represented by General Formula (S), a dicarboxylic acid product which is a precursor of the compound represented by General Formula (B) is obtained, and in a case where two equivalents thereof are reacted with (introduced into) the compound represented by General Formula (S), a dicarboxylic acid product which is a precursor of the compound represented by General Formula (A) is obtained.

The ring $Ar^1$, the ring $Ar^2$, $R^1$, $R^2$, v, and w in General Formula (S) have the same meanings as the ring $Ar^1$, the ring $Ar^2$, $R^1$, $R^2$, v, and w in General Formula (A) or (B).

General Formula (S)

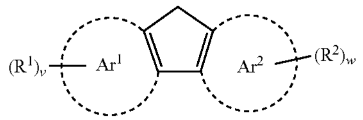

[Curable Resin Composition]

The curable resin composition according to the embodiment of the present invention contains the compound represented by General Formula (A) or (B). By curing the curable resin composition according to the embodiment of the present invention, it is possible to obtain a cured product having both a low Abbe number and a high transmittance.

A content of the compound represented by General Formula (A) or (B) in the curable resin composition according to the embodiment of the present invention can be, for example, 40% by mass or more, and from the viewpoint of further improving nD (refractive index at a wavelength of 589 nm) and further decreasing the Abbe number (νD), the content thereof is preferably 50% by mass or more, more preferably 70% by mass or more, and still more preferably 80% by mass or more. The upper limit value of the above-described content of the compound represented by General Formula (A) or (B) is not particularly limited, and for example, the upper limit value thereof can be 99% by mass or less, and is preferably 97% by mass or less and more preferably 95% by mass or less.

In the curable resin composition according to the embodiment of the present invention, in a case where the content of the compound represented by General Formula (A) or (B) is high, a viscosity of the curable resin composition can be lowered even in a case of being 70% by mass or more, which is preferable.

Two or more kinds of the compounds represented by General Formula (A) or (B) may be contained in the above-described curable resin composition. In a case of containing two or more kinds of the compounds represented by General Formula (A) or (B), the total content thereof is preferably within the above-described range.

<Other Components>

The curable resin composition according to the embodiment of the present invention may further include other components in addition to the compound represented by General Formula (A) or (B). Examples of the other components include a (meth)acrylate monomer, a polymer having a radically polymerizable group in the side chain, and a polymerization initiator.

((Meth)Acrylate Monomer)

The curable resin composition according to the embodiment of the present invention may include a (meth)acrylate monomer. The (meth)acrylate monomer may be a polyfunctional (meth)acrylate monomer having two or more (meth)acryloyl groups in the molecule, or may be a monofunctional (meth)acrylate monomer having one (meth)acryloyl group in the molecule.

Specific examples of the (meth)acrylate monomer include the following monomers 1 to 5 and M-1 to M-10. n in the following monomer 5 means a repetition number. In addition, examples thereof include (meth)acrylate monomers described in paragraphs 0037 to 0046 of JP2012-107191A.

A molecular weight of the (meth)acrylate monomer is preferably 100 to 500.

Monomer 1

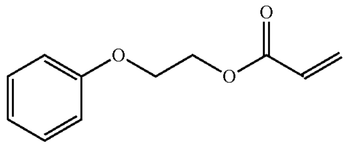

Monomer 2

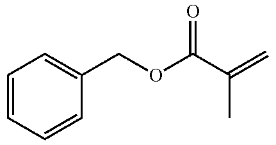

Monomer 3

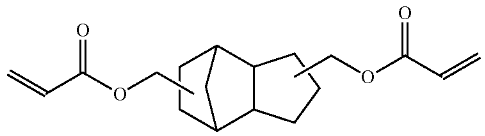

Monomer 4

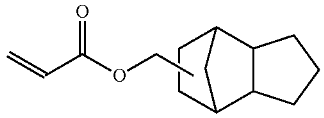

Monomer 5

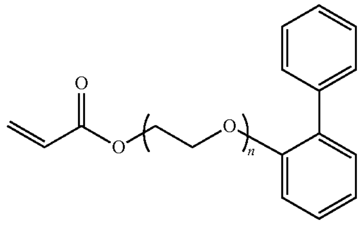

n = 1-2

-continued (M-1)

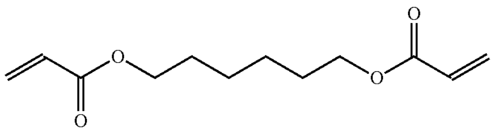

(M-2)

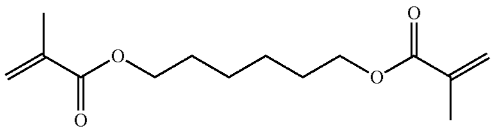

(M-3)

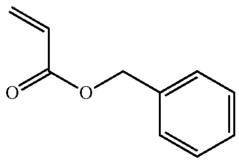

(M-4)

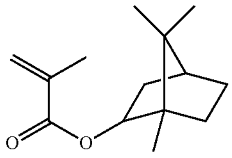

(M-5)

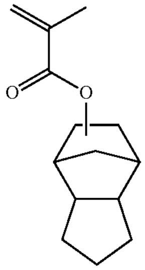

(M-6)

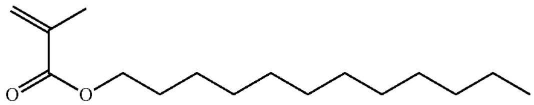

(M-7)

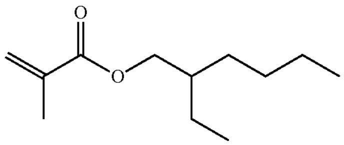

(M-8)

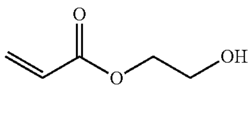

(M-9)

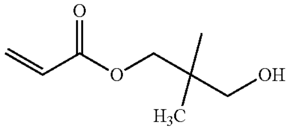

(M-10)

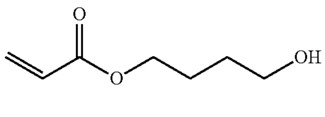

A method for obtaining the (meth)acrylate monomer is not particularly limited, and the (meth)acrylate monomer may be obtained commercially or may be synthesized by a conventional method.

In a case of being obtained commercially, for example, Viscoat #192 PEA (monomer 1 described above) (manufactured by OSAKA ORGANIC CHEMICAL INDUSTRY LTD.), Viscoat #160 BZA (monomer 2 described above) (manufactured by OSAKA ORGANIC CHEMICAL INDUSTRY LTD.), Lightester Bz (monomer 2 described above) (manufactured by KYOEISHA CHEMICAL Co., LTD.), A-DCP (monomer 3 described above) (manufactured by Shin-Nakamura Chemical Co., Ltd.), FA-513AS (monomer 4 described above) (manufactured by Hitachi Chemical Co., Ltd.), A-HD-N (M-1 described above) (manufactured by Shin-Nakamura Chemical Co., Ltd.), HD-N (M-2 described above) (manufactured by Shin-Nakamura Chemical Co., Ltd.), FA-BZA (M-3 described above) (manufactured by Hitachi Chemical Co., Ltd.), Lightester IB-X (M-4 described above) (manufactured by KYOEISHA CHEMICAL Co., LTD.), FA-513M (M-5 described above) (manufactured by Hitachi Chemical Co., Ltd.), Lightester L (M-6 described above) (manufactured by KYOEISHA CHEMICAL Co., LTD.), 2EHA (M-7 described above) (manufactured by TOAGOSEI CO., LTD.), HEA (M-8 described above) (manufactured by OSAKA ORGANIC CHEMICAL INDUSTRY LTD.), Lightester HOP-A(N) (M-9 described above) (manufactured by KYOEISHA CHEMICAL Co., LTD.), or 4-HBA (M-10 described above) (manufactured by OSAKA ORGANIC CHEMICAL INDUSTRY LTD.), all of which are product names, can be preferably used.

In a case where the curable resin composition according to the embodiment of the present invention contains a (meth)acrylate monomer, a content of the (meth)acrylate monomer in the curable resin composition is preferably 1% to 60% by mass, more preferably 2% to 45% by mass, still more preferably 3% to 35% by mass, particularly preferably 5% to 30% by mass, and most preferably 7% to 25% by mass. By adjusting the amount of the (meth)acrylate monomer in the curable resin composition, it is possible to adjust a function of relieving a stress in a case where the cured product undergoes a thermal change.

(Polymer Having Radically Polymerizable Group in Side Chain)

The curable resin composition according to the embodiment of the present invention may further include a polymer having a radically polymerizable group in a side chain, in addition to the above-described compounds. The polymer having a radically polymerizable group in the side chain has a function of increasing the viscosity of the curable resin composition, so that the polymer can also be called a thickener or a thickening polymer. The polymer having a radically polymerizable group in the side chain can be added to adjust the viscosity of the curable resin composition.

The polymer having a radically polymerizable group in the side chain may be a homopolymer or a copolymer. Among these, the polymer having a radically polymerizable group in the side chain is preferably a copolymer. In a case where the polymer having a radically polymerizable group in the side chain is a copolymer, it is sufficient that at least one of copolymerization components has a radically polymerizable group. In addition, in a case where the polymer having a radically polymerizable group in the side chain is a copolymer, a copolymer which includes a monomer unit having a radically polymerizable group in its side chain and a monomer unit having an aromatic hydrocarbon ring group in its side chain is more preferable.

The above-described copolymer may be a copolymer in any form such as random or block.

Examples of the radically polymerizable group include a (meth)acrylate group, a vinyl group, a styryl group, and an allyl group. In the polymer having a radically polymerizable group in the side chain, a structural unit having a radically polymerizable group is included in an amount of preferably 5% to 100% by mass, more preferably 10% to 90% by mass, and still more preferably 20% to 80% by mass.

Hereinafter, specific examples of the polymer having a radically polymerizable group in the side chain, which is preferably used in the present invention, will be shown, but the polymer having a radically polymerizable group in the side chain is not limited to the following structures. Specific examples shown below are all copolymers and include two or three structural units described as being adjacent to each other. For example, a specific example described at the left end of the uppermost stage is a copolymer of allyl methacrylate and benzyl methacrylate.

In the following structural formulae, Ra and Rb each independently represent a hydrogen atom or a methyl group. A plurality of Ra's in one polymer may be the same or different from each other. In addition, n represents 0 to 10, and is preferably 0 to 2 and more preferably 0 or 1. An amount ratio of each structural unit in the copolymer is not particularly limited, and as the content of the structural unit having a radically polymerizable group in the copolymer, the above description can be preferably applied.

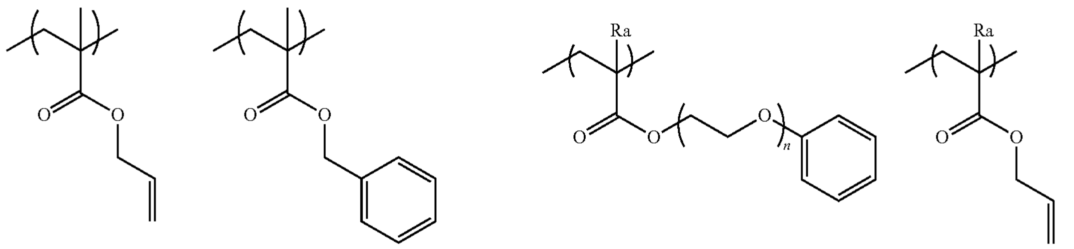

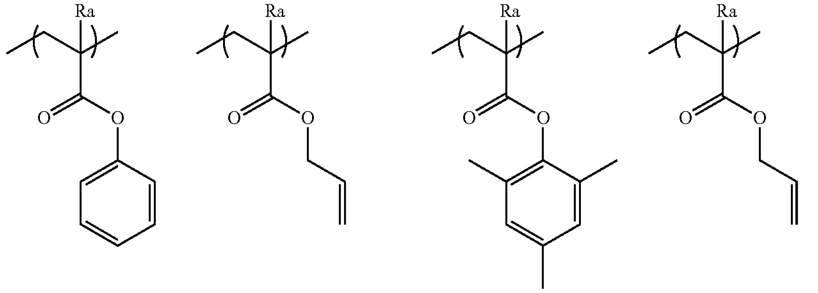

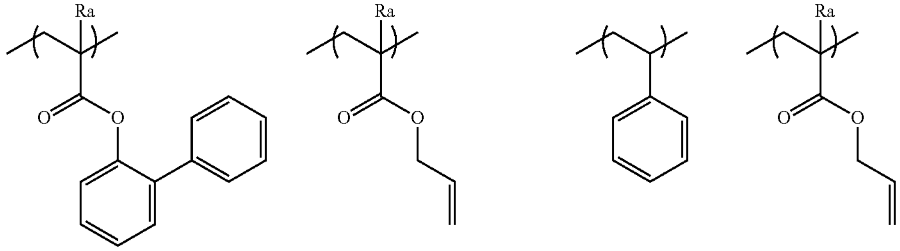

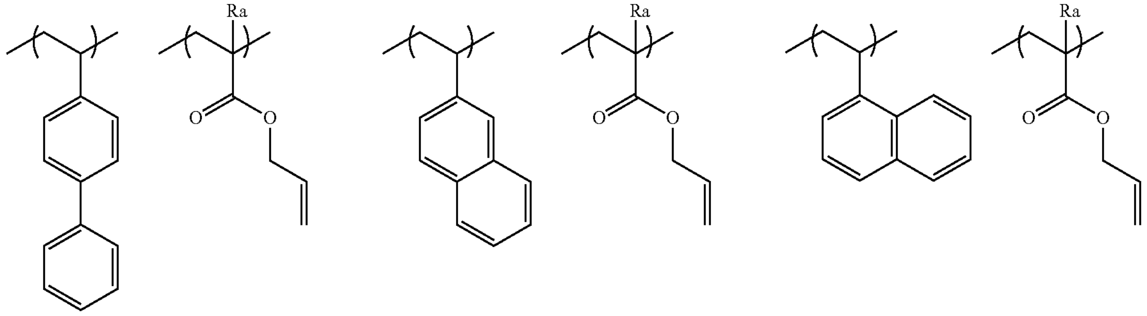

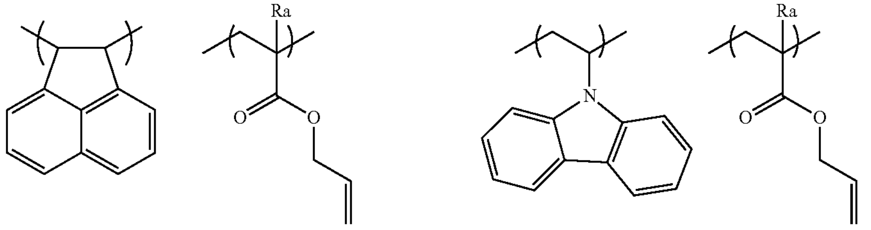

-continued
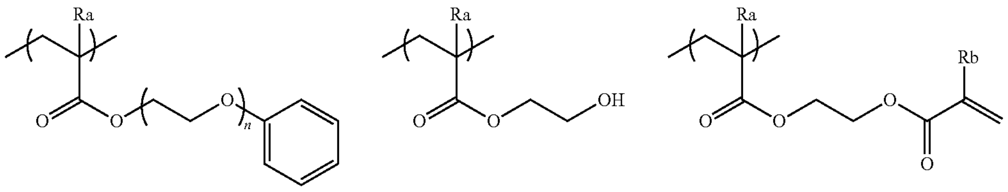
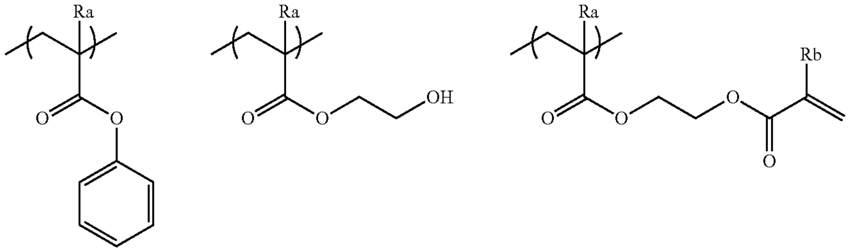
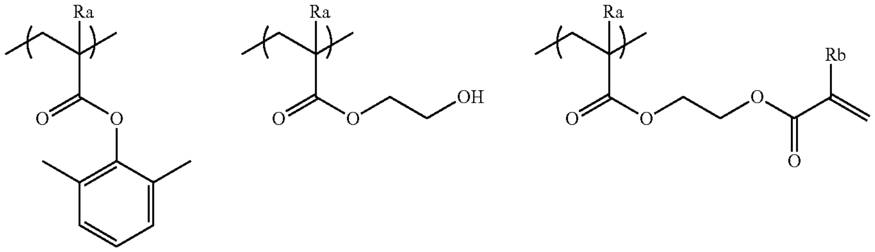
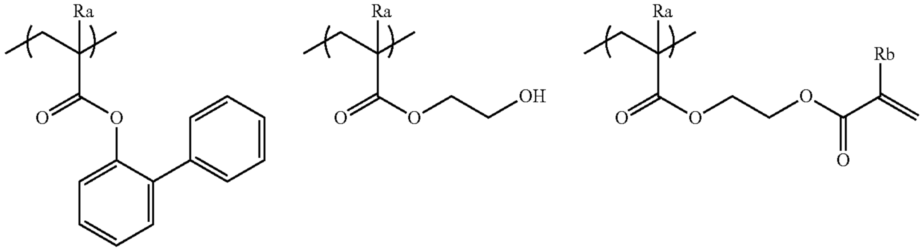
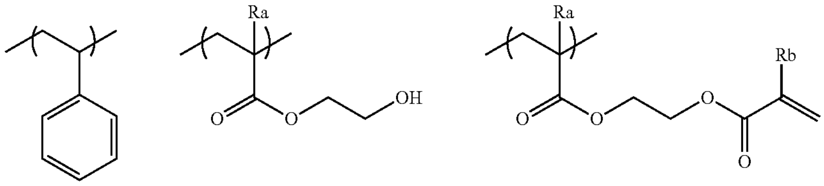
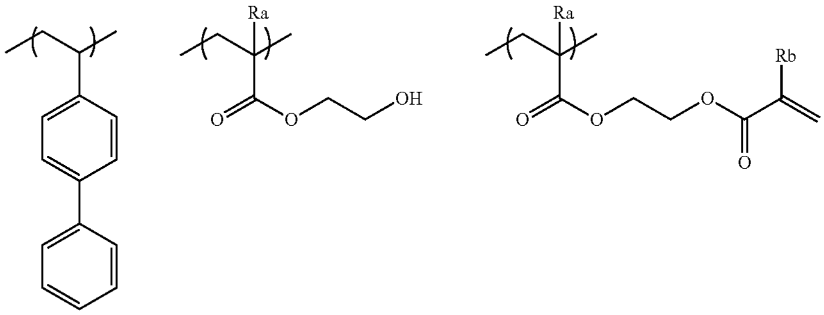
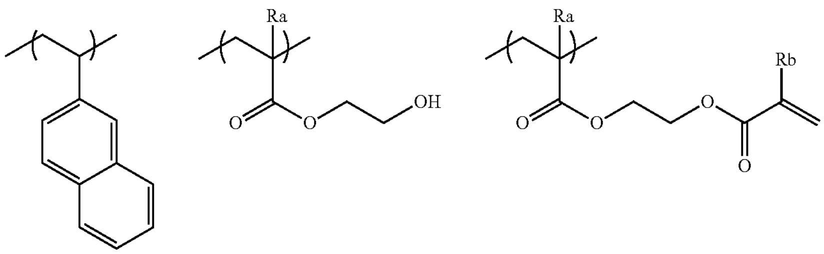

-continued
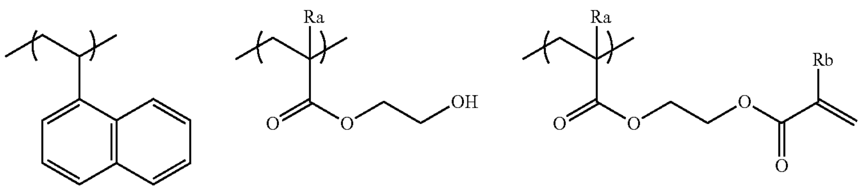
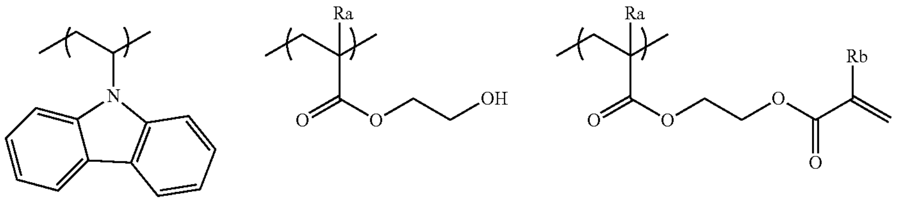
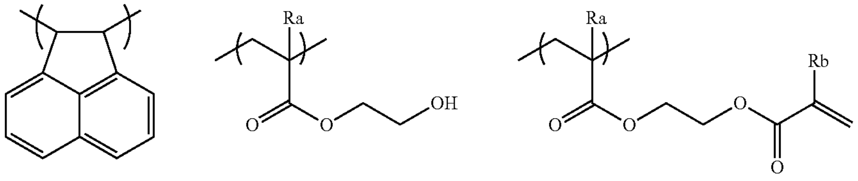
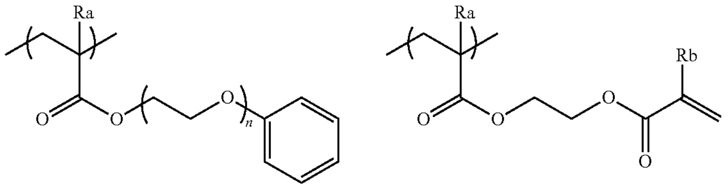
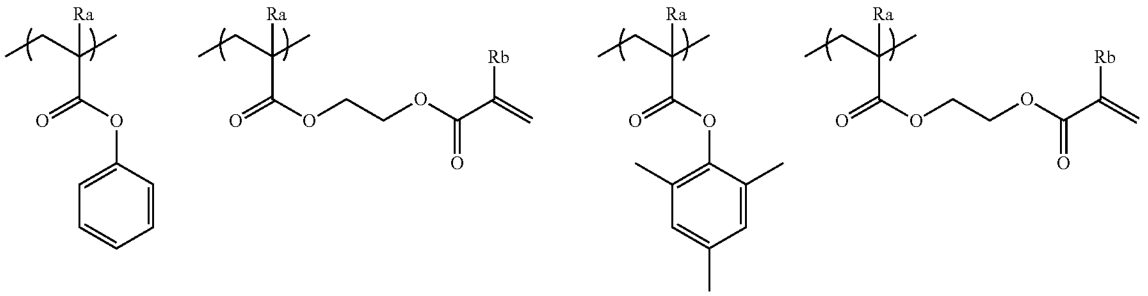
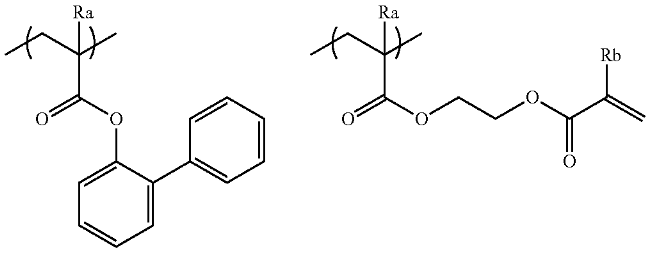
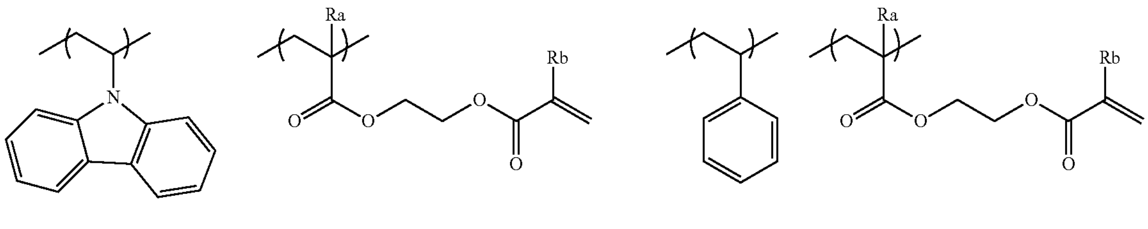

-continued

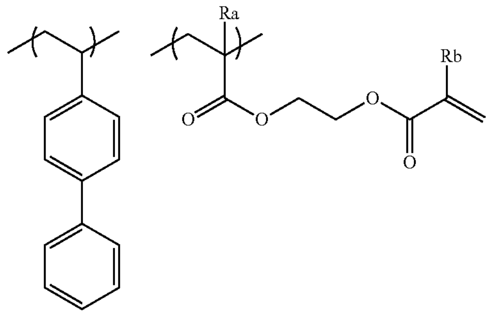

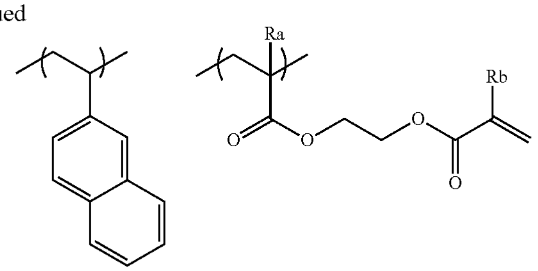

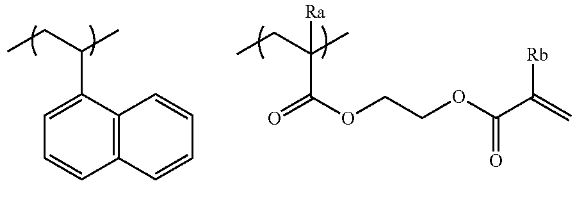

A molecular weight (weight-average molecular weight) of the polymer having a radically polymerizable group in the side chain is preferably 1,000 to 10,000,000, more preferably 5,000 to 300,000, and still more preferably 10,000 to 200,000. A dispersibility (Mw/Mn) of the polymer having a radically polymerizable group in the side chain is preferably 1.1 to 10.0, more preferably 1.3 to 8.0, and still more preferably 1.5 to 6.0. The above-described dispersibility is calculated by dividing the weight-average molecular weight (Mw) by a number-average molecular weight Mn.

The weight-average molecular weight and the dispersibility of the polymer having a radically polymerizable group in the side chain are values measured by GPC in terms of standard polystyrene as described in Examples later.

In addition, a glass transition temperature of the polymer having a radically polymerizable group in the side chain is preferably 50° C. to 400° C., more preferably 70° C. to 350° C., and still more preferably 100° C. to 300° C.

A content of the polymer having a radically polymerizable group in the side chain in the curable resin composition is preferably 40% by mass or less, more preferably 30% by mass or less, still more preferably 25% by mass or less, and particularly preferably 15% by mass or less. The content of the polymer having a radically polymerizable group in the side chain may be 0% by mass, and an aspect in which no polymer having a radically polymerizable group in the side chain is added is also preferable.

(Polymerization Initiator)

The curable resin composition according to the embodiment of the present invention preferably includes, as the polymerization initiator, at least one of a thermal radical polymerization initiator or a photoradical polymerization initiator.

(Thermal Radical Polymerization Initiator)

The curable resin composition according to the embodiment of the present invention preferably includes a thermal radical polymerization initiator. By the action of the thermal polymerization initiator, a cured product exhibiting a low Abbe number and a high transmittance can be obtained by thermally polymerizing the curable resin composition according to the embodiment of the present invention.

As the thermal radical polymerization initiator, a compound usually used as a thermal radical polymerization initiator can be appropriately used according to conditions of a thermopolymerization (heat curing) step described later. Examples thereof include organic peroxides, and specifically, the following compounds can be used.

Examples thereof include 1,1-di(t-hexylperoxy) cyclohexane, 1,1-di(t-butylperoxy) cyclohexane, 2,2-di(4,4-di-(t-butylperoxy)cyclohexyl) propane, t-hexylperoxyisopropyl monocarbonate, t-butylperoxy-3,5,5-trimethylhexanoate, t-butylperoxylaurate, dicumyl peroxide, di-t-butyl peroxide, t-butylperoxy-2-ethylhexanoate, di-tert-hexylperoxide, t-hexylperoxy-2-ethylhexanoate, cumene hydroperoxide, t-butyl hydroperoxide, t-butylperoxy-2-ethylhexyl, and 2,3-dimethyl-2,3-diphenylbutane.

In a case of including a thermal radical polymerization initiator, a content of the thermal radical polymerization initiator in the curable resin composition according to the embodiment of the present invention is preferably 0.01% to 5.0% by mass, more preferably 0.02% to 3.0% by mass, still more preferably 0.03% to 2.0% by mass, and particularly preferably 0.05% to 1.0% by mass.

(Photoradical Polymerization Initiator)

The curable resin composition according to the embodiment of the present invention preferably includes a photoradical polymerization initiator. As the photoradical polymerization initiator, a compound usually used as a photoradical polymerization initiator can be appropriately used according to conditions of a photopolymerization (photocuring) step described later, and specifically, the following compounds can be used.

Examples thereof include bis(2,6-dimethoxybenzoyl)-2,4,4-trimethylpentyl phosphine oxide, bis(2,6-dimethylbenzoyl)-2,4,4-trimethylpentyl phosphine oxide, bis(2,4,6-trimethylbenzoyl)-2,4,4-trimethylpentyl phosphine oxide, bis(2,6-dichlorobenzoyl)-2,4,4-trimethylpentyl phosphine oxide, 1-phenyl-2-hydroxy-2-methylpropan-1-one, 1-hydroxycyclohexylphenylketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)-butanone-1,2,4,6-trimethylbenzoyl-diphenyl-phosphine oxide, and bis(2,4,6-trimethylbenzoyl)-phenylphosphine oxide.

Among the photoradical polymerization initiators mentioned above, an acylphosphine oxide photopolymerization initiator is preferable from the viewpoint of obtaining a cured product having excellent light resistance.

Among these, in the present invention, as the photoradical polymerization initiator, 1-hydroxycyclohexylphenylketone (available as Irgacure 184 (product name) from BASF), bis(2,4,6-trimethylbenzoyl)-phenylphosphine oxide (available as Irgacure 819 (product name) from BASF), 2,4,6-trimethylbenzoyl-diphenyl-phosphinoxide (available as Irgacure TPO (product name) from BASF), 2,2,-dimethoxy-1,2-diphenylethan-1-one (available as Irgacure 651 (product name) from BASF), 1-[4-(2-hydroxyethoxy)-phenyl]-2-hydroxy-2-methyl-1-propan-1-one, or 2-methyl-1-(4-methylthiophenyl)-2-morpholinopropan-1-one can be preferably used.

In a case of containing a photoradical polymerization initiator, a content of the photoradical polymerization initiator in the above-described curable resin composition is preferably 0.01% to 5.0% by mass, more preferably 0.05% to 1.0% by mass, and still more preferably 0.05% to 0.5% by mass.

The curable resin composition according to the embodiment of the present invention preferably includes both the photoradical polymerization initiator and the thermal radical polymerization initiator. In this case, the total content of the photoradical polymerization initiator and the thermal radical polymerization initiator is preferably 0.01% to 5.0% by mass, more preferably 0.05% to 1.0% by mass, and still more preferably 0.05% to 0.5% by mass with respect to the total mass of the curable resin composition.

The curable resin composition including the compound represented by General Formula (A) or (B) may include a polymer or a monomer other than the above-described components, a dispersant, a plasticizer, a heat stabilizer, a release agent, a solvent, or the like as long as the gist of the invention is maintained.

From the viewpoint of improving handleability in a case of molding the cured product and forming a high-quality cured product, a viscosity of the curable resin composition including the compound represented by General Formula (A) or (B) is preferably 1000 to 30000 mPa s, more preferably 3000 to 20000 mPa s, and still more preferably 5000 to 15000 mPa s. The above-described viscosity of the curable resin composition is a viscosity measured by a method described in Examples later. 1 mPa s is 1 cP.

[Cured Product]

A cured product according to an embodiment of the present invention is a cured product of the above-described curable resin composition including the compound represented by General Formula (A) or (B).

The cured product according to the embodiment of the present invention is obtained by advancing a polymerization reaction of a monomer including the compound represented by General Formula (A) or (B) and curing the monomer. The cured product according to the embodiment of the present invention may include an unreacted monomer (for example, the compound represented by General Formula (A) or (B)) and the like.

As described above, in the cured product according to the embodiment of the present invention, the trade-off relationship between the Abbe number νD and the transmittance is improved with respect to cured products obtained from compounds in the related art, and both a low Abbe number νD and a high transmittance can be achieved at an excellent level.

An Abbe number (νD) and a partial dispersion ratio (θg, F) of the cured product are values measured using an Abbe refractionometer (manufactured by ATAGO CO., LTD., product name: DR-M4). Specifically, the curable resin composition is poured into a transparent glass mold having a diameter of 20 mm and a thickness of 1 mm, and irradiated with ultraviolet rays of 1000 mJ/cm$^2$ from above the transparent glass mold in an atmosphere having an oxygen concentration of 1% or less to mold a cured product (a ultraviolet irradiating step), and an Abbe number (νD) and a partial dispersion ratio (θg, F) of this cured product are measured. The Abbe number (νD) and the partial dispersion ratio (θg, F) of the cured product are calculated by the following expressions. In a case of molding a cured product, a heating step may be employed instead of the above-described ultraviolet irradiating step, or both of the heating step and the ultraviolet irradiating step may be employed. In addition, JIS B 7090:1999 optics and optical equipment-reference wavelengths (ISO 7944:1998 Optics and optical instruments-Reference wavelengths) can be appropriately referred to.

$$\nu D=(nD-1)/(nF-nC)$$

$$\theta g,F=(ng-nF)/(nF-nC)$$

Here, nD represents a refractive index at a wavelength of 589 nm, nF represents a refractive index at a wavelength of 486 nm, nC represents a refractive index at a wavelength of 656 nm, and ng represents a refractive index at a wavelength of 436 nm.

nD of the cured product according to the embodiment of the present invention is not particularly limited, but is preferably 1.590 or more, more preferably 1.595 or more, and still more preferably 1.600 or more. The upper limit value of nD of the cured product according to the embodiment of the present invention is not particularly limited, but is practically 1.680 or less.

The Abbe number νD of the cured product according to the embodiment of the present invention is preferably 22.0 or less, more preferably 21.0 or less, and still more preferably 20.0 or less. In addition, the lower limit value of the Abbe number of the cured product according to the embodiment of the present invention is not particularly limited, but it is preferably 1 or more, more preferably 3 or more, still more preferably 5 or more, and particularly preferably 7 or more.

The partial dispersion ratio (θg, F) of the cured product according to the embodiment of the present invention is not particularly limited, but is preferably 0.65 or more, more preferably 0.70 or more, still more preferably 0.75 or more, and from the viewpoint of being particularly suitably used as a lens resin having high chromatic aberration correction power in a blue region, particularly preferably 0.80 or more. In addition, the upper limit value of the partial dispersion ratio (θg, F) of the cured product according to the embodiment of the present invention is not particularly limited, but it is preferably 2.0 or less, more preferably 1.8 or less, and still more preferably 1.7 or less.

A transmittance of the cured product according to the embodiment of the present invention is preferably 65.0% or more, more preferably 70.0% or more, and still more preferably 80.0% or more. The upper limit value of the transmittance of the cured product according to the embodiment of the present invention is not particularly limited, but is practically 89% or less.

The above-described transmittance of the cured product is a transmittance at a wavelength of 420 nm, which is measured using an ultraviolet-visible spectrophotometer by a method described in Examples later, and is a value of an external transmittance including surface reflection.

A birefringence Δn of the cured product according to the embodiment of the present invention at a wavelength of 543 nm (hereinafter, also referred to as a birefringence Δn(543 nm)) is preferably 0.00≤Δn≤0.01. The birefringence Δn(543 nm) is preferably 0.001 or less and more preferably less than 0.001. By using a cured product having such a low birefringence index for an optical member of an imaging module, it is possible to obtain a clear image in which an imaging position is unlikely to shift. The lower limit value of the birefringence Δn(543 nm) may be 0.00001 or 0.0001.

The birefringence Δn(543 nm) of the cured product can be obtained by the following method. A film-shaped sample is produced, and using a birefringence evaluation device (for example, WPA-100, manufactured by Photonic Lattice, Inc.), a birefringence within a 10 mm diameter circle including the center of the sample is measured. Thereafter, the birefringence Δn(543 nm) can be obtained by obtaining the average value of birefringence at a wavelength of 543 nm.

A glass transition temperature (Tg) of the cured product according to the embodiment of the present invention is not particularly limited, but it is preferably 40° C. to 200° C. and more preferably 50° C. to 180° C.

The above-described glass transition temperature is a value measured by the following method.

(1) Production of cured product sample for glass transition temperature measurement The curable resin composition according to the embodiment of the present invention is placed on a rectangular hydrophobized glass plate having a length of 8 cm and a width of 5 cm, and the glass plate is sandwiched between glass plates of the same size such that a thickness is 150 μm to spread the curable resin composition.

In an atmosphere with an oxygen concentration of 1% or less, using EXECURE 3000 (product name, manufactured by HOYA CORPORATION) as a UV irradiation device, the curable resin composition is irradiated with ultraviolet rays of 2 $J/cm^2$, and the glass plate is removed to obtain a cured product single film (cured product sample for glass transition temperature measurement).

(2) Dynamic Viscoelasticity Measurement

The above-described cured product sample is cut into a rectangular size of a length of 2.2 cm and a width of 0.5 cm, and using a dynamic viscoelasticity measuring device (manufactured by UBM Co., Ltd.), a storage elastic modulus (E'), loss elastic modulus (E"), and loss tangent (tan δ) are measured from −50° C. to 150° C. at a frequency of 10 Hz. The temperature of the main dispersion of tan δ is defined as Tg.

[Method for Manufacturing Cured Product]

The cured product according to the embodiment of the present invention can be manufactured by a method including at least one of a step of photocuring the above-described curable resin composition or a step of thermosetting the above-described curable resin composition. Among these, a method for manufacturing the cured product preferably includes a step of forming a semi-cured product by irradiating the curable resin composition with light or heating the curable resin composition; and a step of forming a cured product by irradiating the obtained semi-cured product with light or heating the obtained semi-cured product. The "forming" is used to include obtaining a cured product in addition to the actual forming.

As each of the "step of forming a semi-cured product", the "step of forming a cured product", and the "semi-cured product", the description of the "step of forming a semi-cured product", the "step of forming a cured product", and the "semi-cured product" in [0106] to [0117], [0118] to [0124], and [0125] of WO2019/044863A can be adopted as they are.

[Use of Cured Product]

Since the cured product according to the embodiment of the present invention exhibits a low Abbe number (νD) and a high transmittance, the cured product can be used for various uses, and among these, the cured product can be preferably used for an optical member.

[Optical Member]

A type of optical member is not particularly limited, but the cured product of the embodiment of the present invention can be suitably used especially for light-transmissive optical members (so-called passive optical members). Examples of optically-functional devices including such optical members include various types of display devices (a liquid crystal display, a plasma display, and the like), various types of projector devices (an overhead projector (OHP), a liquid crystal projector, and the like), optical fiber communication devices (an optical waveguide, a light amplifier, and the like), image-capturing devices such as a camera and a video, and the like.

Examples of passive optical members include lenses, prisms, prism sheets, panels (plate-like molded objects), films, optical waveguides (a film-like optical waveguide, a fiber-like optical waveguide, and the like), optical discs, light emitting diode (LED) sealants, and the like. The passive optical member may have an optionally coating layer or an optionally additional functional layer as necessary. For example, the passive optical member may have a protective layer for preventing mechanical damage of a coating surface caused by friction or abrasion; a light-absorbing layer for absorbing a light having an undesirable wavelength which is a cause of degradation of inorganic particles, base materials, and the like; a permeation blocking layer for inhibiting or preventing permeation of reactive small molecules such as moisture or oxygen gas; an anti-glare layer; an antireflection layer; a layer of low refractive index; and the like. Specific examples of coating layers include a transparent conductive film or gas barrier film consisting of an inorganic oxide coating layer or inorganic nitride coating layer, a gas barrier film or hard coat film consisting of an organic coating layer, and the like. As a coating method for forming the coating layer, it is possible to use a known coating method such as a vacuum deposition method, a CVD method, a sputtering method, a dip coating method, and a spin coating method.

[Lens Base Material]

The optical member may be a lens base material. That is, the cured product according to the embodiment of the present invention may be used as a lens base material. In the present invention, the "lens base material" refers to a single member capable of exhibiting a lens function. The lens base material manufactured using the cured product according to the embodiment of the present invention exhibits a low Abbe number and a high transmittance. Preferably, by suitably adjusting the type of monomer constituting the curable resin composition, it is possible to control a refractive index of the lens base material in an arbitrary value, and furthermore, it is possible to obtain the lens base material having high refractive properties, high partial dispersion ratio, and lightweight properties.

A film or a member can be provided on the surface or the periphery of the lens base material depending on the environment in which the lens is used or the use of the lens. For example, a protective film, an anti-reflection film, a hard coat film, and the like can be formed on the surface of the lens base material. In addition, a lens base material manufactured using the cured product according to the embodiment of the present invention can be made into a composite lens laminated with one or more other lens base materials (hereinafter, referred to as "other lens base materials") selected from a glass lens base material and a plastic lens base material.

For example, such a composite lens can be manufactured by a method in which a semi-cured product is formed by photo-curing the curable resin composition according to the embodiment of the present invention on the other lens base materials, and the obtained semi-cured product is heated to form a cured product. The above description can be preferably applied to each of the semi-curing step and the step of forming the cured product. Since the curable resin composition according to the embodiment of the present invention has excellent photocuring sensitivity, it is possible to obtain a composite lens having excellent quality.

The periphery of the lens base material may be fitted into be fixed in a base-material-holding frame or the like. However, these films, frames, and the like are members added to the lens base material, and are distinguished from the lens base material itself in the present invention.

The lens according to the embodiment of the present invention includes the cured product according to the embodiment of the present invention. Specifically, in a case of using the above-described lens base material for lenses, the lens base material itself may be used as a lens by itself, or additional films or frames or additional lens base materials may be added thereto for use as a lens, as described above. The type and a shape of a lens formed of the lens base material are not particularly limited, but the maximum thickness thereof is preferably 0.1 to 10 mm. The maximum thickness is more preferably 0.1 to 5 mm and still more preferably 0.15 to 3 mm. In addition, the lens base material is preferably a circular shape having the maximum diameter of 1 to 1000 mm. The maximum diameter thereof is more preferably 2 to 200 mm and still more preferably 2.5 to 100 mm.

The lens base material is preferably used as an image pick-up lens in a mobile phone, a digital camera, or the like, an imaging lens in a television, a video camera, or the like, and an in-vehicle lens or an endoscopic lens.

<Cemented Lens>

A cemented lens can be manufactured by adhering the lens base material or the lens manufactured using the curable resin composition according to the embodiment of the present invention to another lens using a lens adhesive.

As the lens adhesive, a commonly used adhesive can be used without limitation, and for example, the lens adhesive described in WO2019/131572A can be used.

[Other Lenses]

The type of other lenses is not particularly limited, and examples thereof include a disk-shaped convex lens, a concave lens, a meniscus lens, an aspherical lens, a cylindrical lens having a cylindrical lens surface, a ball lens, and a rod lens. In addition, a material of the other lenses is not particularly limited as long as it is a glass lens, a resin lens, or a composite lens.

(Glass Lens)

As the glass lens, commonly used glass lens can be used without limitation. Examples of a commercially available glass lens include BK7 (product name) manufactured by OHARA INC.

The same glass lens can be used in a case where the composite lens includes a glass lens.

(Resin Lens and Composite Lens)

The resin lens means a lens made of a resin cured product.

In the present invention, the composite lens means a lens including a layer made of glass and a resin layer. The resin layer is a layer made of a resin cured product. Each layer included in the composite lens may be a lens (single lens), and in this case, it is preferable that optical axes of the single lenses (lines connecting centers of curvature of both spherical surfaces) are aligned. The composite lens may have a resin layer on the surface thereof or may have a resin layer inside the composite lens.

EXAMPLES

Hereinafter, the present invention will be described in more detail based on Examples. The materials, amounts used, proportions, treatment details, treatment procedures, and the like described in the following examples can be appropriately modified as long as the gist of the invention is maintained. Therefore, the scope of the present invention should not be construed as being limited to the following specific examples.

All steps from the preparation of the curable resin composition to the test of the cured product were carried out in an environment where a yellow lamp was used as lighting.

Synthesis Example

The compound represented by General Formula (A) or General Formula (B) was synthesized as follows.

The abbreviations used in the synthesis of each compound described below indicate the following compounds. In addition, w/v % means a mass-to-volume percentage, and room temperature means 25° C.

EDAC.HCl: 1-ethyl-3-(3-dimethylaminopropyl)carbodiimide hydrochloride

MEK: methyl ethyl ketone

THF: tetrahydrofuran

Et: ethyl group

An HPLC measurement and a transmittance measurement were carried out according to measuring methods shown below.

(HPLC Measurement)

Using a high-speed liquid chromatography (product name: SPD-10AV VP) manufactured by Shimadzu Corporation, a purity of the compound was measured under the following conditions. In a case where the compound was added to a solvent, a peak derived from the solvent was subtracted, and then the HPLC purity was obtained.

Column: TSKgel ODS-100Z 5 m (4.6 mmφ×150 mm) (manufactured by Tosoh Corporation)

Column temperature: 40° C.

Eluent: acetonitrile:pure water:phosphoric acid (volume ratio)=700:300:1

Flow Rate: 1.0 ml/min

Detection wavelength: 254 nm

Injection amount: 10 μL

Sample: compound was dissolved in the eluent so as to have a concentration of 5 mg/50 ml.

(Transmittance Measurement)

Using a spectrophotometer (product name: UV-2550) manufactured by Shimadzu Corporation, a transmittance of the compound at a wavelength of 420 nm was measured under the following conditions. As the transmittance at 420 nm is higher, coloration is less likely to occur.

Cell: square quartz cell (optical path length: 1 cm)

Sample: compound was dissolved in THF so as to have a concentration of 50 mg/5 mL.

Blank: THF (solvent)

[1. Synthesis of Raw Material Compounds (A1) to (A5)]

Raw material compounds (A1) to (A5) were synthesized as follows after synthesizing compounds (SA-1) to (SA-5).

Synthesis of Compound (SA-1)

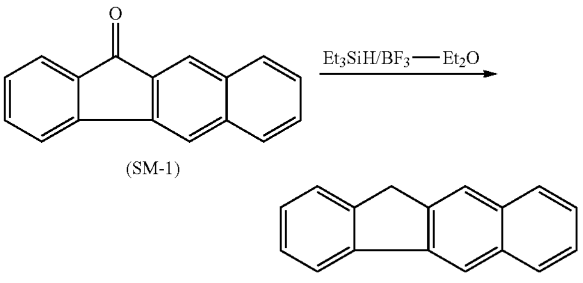

(SM-1)

(SA-1)

15.0 g of 11H-benzo[b]fluoren-11-one (SM-1) and 60 mL of methylene chloride were charged into a 500 mL three-neck flask, and 60 mL of trifluoroacetic acid and 22.8 g of triethylsilane were added thereto while cooling the mixture in an ice bath. Subsequently, 18.6 g of a boron trifluoride-diethyl ether complex was added dropwise thereto over 30 minutes, and then the reaction was carried out at 40° C. for 3 hours. After cooling to room temperature, 180 mL of cyclopentylmethyl ether was added thereto, and the mixture was further stirred for 2 hours. The precipitated solid was recovered by filtration and vacuum-dried in a vacuum oven to obtain 10.3 g of the compound (SA-1) (yield: 73.1%).

Synthesis of Compound (SA-2)

7.2 g of the compound (SA-2) (yield: 82.0%) was obtained in the same manner as in the above-described synthesis of the compound (SA-1), except that the compound (SM-1) was changed to a compound (SM-2).

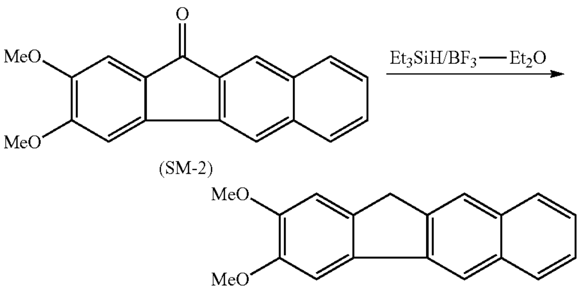

(SM-2)

(SA-2)

Synthesis of Compound (SA-3)

6.0 g of the compound (SA-3) (yield: 63.8%) was obtained in the same manner as in the above-described synthesis of the compound (SA-1), except that the compound (SM-1) was changed to a compound (SM-3).

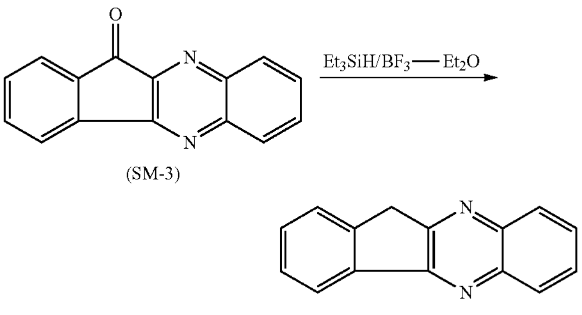

(SM-3)

(SA-3)

Synthesis of Compound (SA-4)

6.2 g of the compound (SA-4) (yield: 66.0%) was obtained in the same manner as in the above-described synthesis of the compound (SA-1), except that the compound (SM-1) was changed to a compound (SM-4).

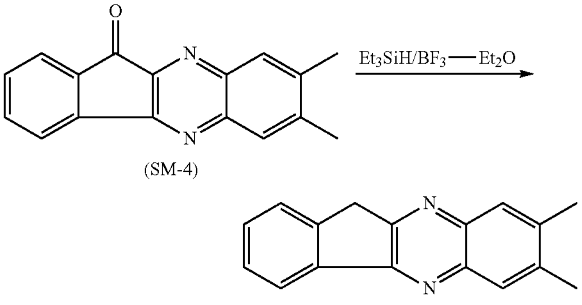

(SM-4)

(SA-4)

Synthesis of Compound (SA-5)

8.2 g of the compound (SA-5) (yield: 86.5%) was obtained in the same manner as in the above-described synthesis of the compound (SA-1), except that the compound (SM-1) was changed to a compound (SM-5).

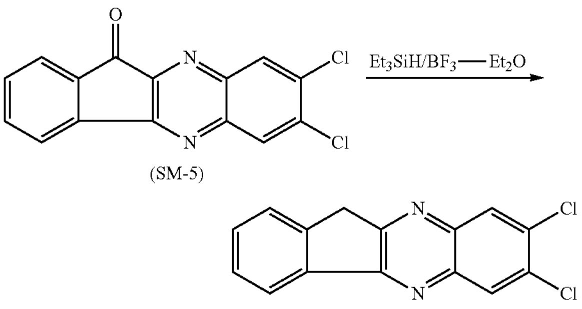

(SM-5)

(SA-5)

Synthesis Example 1-1: Synthesis of Compound (A1)

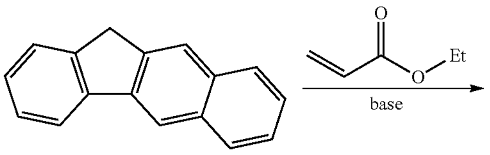

(SA-1)

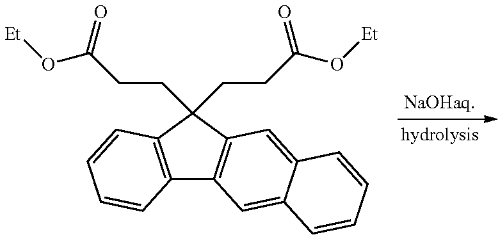

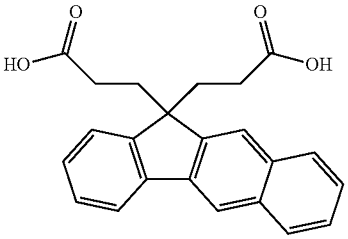

(A1)

5.0 g of the compound (SA-1), 6.9 g of ethyl acrylate, and 50 mL of N,N-dimethylacetamide were charged into a 200 mL three-neck flask, and stirred at room temperature for 10 minutes. 2.9 g of a 40% by mass methanol solution of benzyltrimethylammonium hydroxide was added thereto, and the mixture was reacted at 80° C. for 1 hour. After confirming disappearance of the raw material compound (SA-1) by TLC, 7.5 mL of water and 7.5 mL of a 50 w/v % sodium hydroxide aqueous solution were added thereto, and the mixture was stirred at 80° C. for 1 hour to hydrolyze ethyl ester. After cooling to room temperature, the mixture was neutralized with 6N hydrochloric acid, ethyl acetate was added thereto, and a liquid separation operation was performed. The organic layer was washed with 1N hydrochloric acid and saturated saline, and dried with magnesium sulfate. After removing the magnesium sulfate by filtration, the solvent was concentrated, and the precipitated solid was dispersed and washed with a mixed solvent of ethyl acetate and hexane to obtain 4.8 g of the compound (A1) (yield: 58%). An area % of the compound (A1) determined from the HPLC measurement was 96.6%, and the area of the raw material compound (SA-1) was 0.1% or less. In addition, the transmittance of the compound (A1) at 420 nm was 99.3%.

$^1$H-NMR data of compound (A1) (400 MHz, DMSO-$d_6$): δ 1.35 to 1.45 ppm (m, 4H), 2.35 to 2.45 ppm (m, 4H), 7.35 to 7.60 ppm (m, 5H), 7.90 to 8.10 ppm (m, 4H), 8.35 ppm (s, 1H), 11.9 ppm (s, 2H)

Synthesis Example 1-2: Synthesis of Compound (A2)

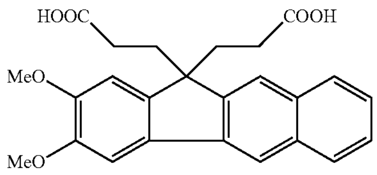

(A2)

4.5 g of the compound (A2) (yield: 59%) was obtained in the same manner as in Synthesis Example 1-1, except that the compound (SA-1) was changed to the compound (SA-2). An area % of the compound (A2) determined from the HPLC measurement was 96.2%, and the raw material compound (SA-2) was 0.1% or less. In addition, the transmittance of the compound (A2) at 420 nm was 99.0%.

$^1$H-NMR data of compound (A2) (400 MHz, DMSO-$d_6$): δ 1.35 to 1.45 ppm (m, 4H), 2.35 to 2.45 ppm (m, 4H), 3.80 ppm (s, 3H), 3.90 ppm (s, 3H), 7.15 ppm (s, 1H), 7.35 to 7.50 ppm (m, 2H), 7.60 ppm (s, 1H), 7.85 to 7.90 ppm (m, 3H), 8.20 ppm (s, 1H), 11.9 ppm (s, 2H)

Synthesis Example 1-3: Synthesis of Compound (A3)

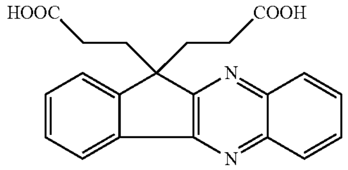

(A3)

5.5 g of the compound (A3) (yield: 70%) was obtained in the same manner as in Synthesis Example 1-1, except that the compound (SA-1) was changed to the compound (SA-3). An area % of the compound (A3) determined from the HPLC measurement was 97.1%, and the raw material compound (SA-3) was 0.1% or less. In addition, the transmittance of the compound (A3) at 420 nm was 99.1%.

$^1$H-NMR data of compound (A3) (400 MHz, DMSO-$d_6$): δ 1.50 to 1.75 ppm (m, 4H), 2.35 to 2.55 ppm (m, 4H), 7.62 ppm (t, 1H), 7.70 ppm (t, 1H), 7.75 to 7.90 ppm (m, 3H), 8.15 to 8.25 ppm (m, 3H), 12.0 ppm (s, 2H)

Synthesis Example 1-4: Synthesis of Compound (A4)

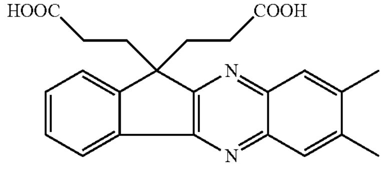

(A4)

6.2 g of the compound (A4) (yield: 78%) was obtained in the same manner as in Synthesis Example 1-1, except that the compound (SA-1) was changed to the compound (SA-4). An area % of the compound (A4) determined from the HPLC measurement was 97.6%, and the raw material compound (SA-4) was 0.1% or less. In addition, the transmittance of the compound (A4) at 420 nm was 98.9%.

$^1$H-NMR data of compound (A4) (400 MHz, DMSO-$d_6$): δ 1.50 to 1.75 ppm (m, 4H), 2.35 to 2.55 ppm (m, 10H), 7.55 ppm (t, 1H), 7.62 ppm (t, 1H), 7.76 ppm (d, 1H), 7.90 to 7.95 ppm (m, 2H), 8.10 ppm (d, 1H), 12.0 ppm (s, 2H)

Synthesis Example 1-5: Synthesis of Compound (A5)

(A5)

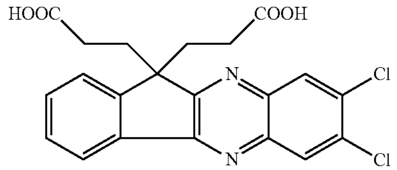

6.7 g of the compound (A5) (yield: 89%) was obtained in the same manner as in Synthesis Example 1-1, except that the compound (SA-1) was changed to the compound (SA-5). An area % of the compound (A5) determined from the HPLC measurement was 95.9%, and the raw material compound (SA-5) was 0.1% or less. In addition, the transmittance of the compound (A5) at 420 nm was 98.7%.

$^1$H-NMR data of compound (A5) (400 MHz, DMSO-$d_6$): δ 1.55 to 1.80 ppm (m, 4H), 2.35 to 2.55 ppm (m, 4H), 7.60 ppm (t, 1H), 7.75 ppm (t, 1H), 7.80 ppm (d, 1H), 8.12 ppm (d, 1H), 8.40 to 8.50 ppm (m, 2H), 12.0 ppm (s, 2H)

[2. Synthesis of Compounds (A1-1) to (A5-1)]

Compounds (A1-1) to (A5-1) represented by General Formula (A) or (B) were synthesized as follows.

Synthesis Example 2-1: Synthesis of Compound (A1-1)

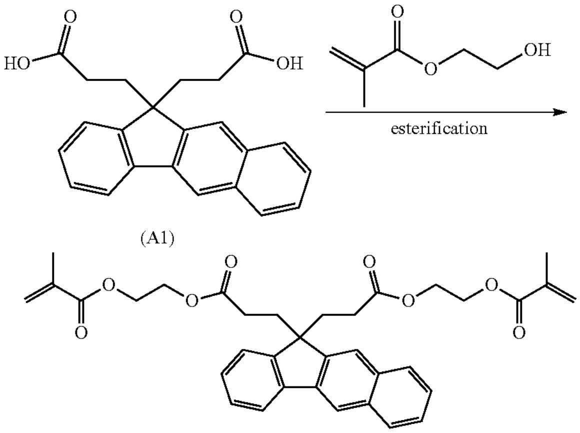

(A1)

(A1-1)

4.0 g of the compound (A1), 20 mL of dichloromethane, 3.3 g of 2-hydroxyethyl methacrylate, 0.1 g of N,N-dimethylaminopyridine, and 4.9 μg of 1-ethyl-3-(3-dimethylaminopropyl)carbodiimide hydrochloride were mixed with each other. After stirring at 40° C. for 2 hours, 1N hydrochloric acid was added thereto, the mixture was washed and liquid-separated, a 5% sodium hydrogen carbonate aqueous solution was added thereto, and the mixture was washed and liquid-separated. After dehydration with magnesium sulfate, filtration, and concentration, purification was performed by column chromatography (eluent: mixed solution of chloroform and methanol) to obtain 5.4 g of the compound (A1-1) (yield: 83%).

$^1$H-NMR of compound (A1-1) (400 MHz, $CDCl_3$): δ=1.65 to 1.85 ppm (m, 4H), 1.89 ppm (s, 6H), 2.45 to 2.55 ppm (m, 4H), 4.15 to 4.25 ppm (m, 8H), 5.55 ppm (s, 2H), 6.05 ppm (s, 2H), 7.35 to 7.55 ppm (m, 6H), 7.78 ppm (s, 1H), 7.82 to 7.95 ppm (m, 2H), 8.15 ppm (s, 1H)

Absorption spectrum (absorbance) of the compound (A1-1) was measured by the following procedure.

The compound was precisely weighed in an amount of 50 mg, diluted with tetrahydrofuran (THF) using a 5 mL volumetric flask, and further diluted with THE so that the solution concentration was 1/500 times to prepare a measurement solution. The measurement was performed using UV-2550 (product name) manufactured by Shimadzu Corporation.

First, a square quartz cell (cell length: 10 mm) containing a control sample (THF) in both the sample optical path and the control optical path was placed, and the absorbance in a wavelength region of 250 to 800 nm was adjusted to zero. Next, the sample in the sample optical path-side cell was replaced with the measurement solution of the compound prepared above, and the absorption spectrum at 250 to 800 nm was measured.

A wavelength λmax of the maximal peak on the longest wavelength side in a range of 300 to 400 nm, which was obtained from the measurement result, was 343 nm.

Synthesis Example 2-2: Synthesis of Compound (A2-1)

(A2-1)

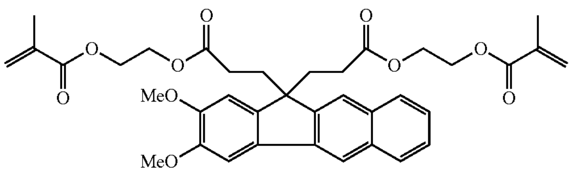

4.9 g of the compound (A2-1) (yield: 80%) was obtained in the same manner as in Synthesis Example 2-1, except that the compound (A1) was changed to the compound (A2).

$^1$H-NMR of compound (A2-1) (400 MHz, $CDCl_3$): δ=1.65 to 1.85 ppm (m, 4H), 1.89 ppm (s, 6H), 2.45 to 2.55 ppm (m, 4H), 3.96 ppm (s, 3H), 4.02 ppm (s, 3H), 4.15 to 4.25 ppm (m, 8H), 5.55 ppm (s, 2H), 6.05 ppm (s, 2H), 6.85 ppm (s, 1H), 7.35 ppm (s, 1H), 7.40 to 7.55 ppm (m, 2H), 7.71 ppm (s, 1H), 7.80 to 7.93 ppm (m, 2H), 8.00 ppm (s, 1H)

A wavelength λmax of the maximum peak of the compound (A2-1) on the longest wavelength side in a range of 300 to 400 nm, which was measured in the same manner as that of the compound (A1-1), was 354 nm.

Synthesis Example 2-3: Synthesis of Compound (A3-1)

(A3-1)

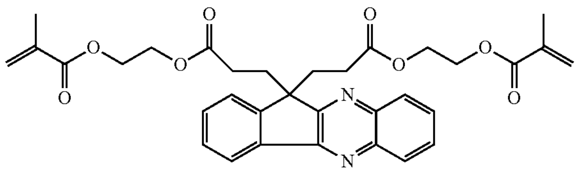

5.2 g of the compound (A3-1) (yield: 80%) was obtained in the same manner as in Synthesis Example 2-1, except that the compound (A1) was changed to the compound (A3).

$^1$H-NMR data of compound (A3-1) (400 MHz, $CDCl_3$): δ=1.65 to 1.85 ppm (m, 4H), 1.89 ppm (s, 6H), 2.38 to 2.48 ppm (m, 2H), 2.68 to 2.78 ppm (m, 2H), 4.15 to 4.25 ppm (m, 8H), 5.55 ppm (s, 2H), 6.05 ppm (s, 2H), 7.55 to 7.65 ppm (m, 3H), 7.80 to 7.95 ppm (m, 2H), 8.10 to 8.25 ppm (m, 3H)

A wavelength λmax of the maximum peak of the compound (A3-1) on the longest wavelength side in a range of 300 to 400 nm, which was measured in the same manner as that of the compound (A1-1), was 360 nm.

Synthesis Example 2-4: Synthesis of Compound (A4-1)

(A4-1)

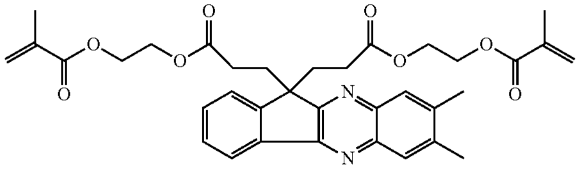

4.4 g of the compound (A4-1) (yield: 70%) was obtained in the same manner as in Synthesis Example 2-1, except that the compound (A1) was changed to the compound (A4).

$^1$H-NMR of compound (A4-1) (400 MHz, $CDCl_3$): δ=1.65 to 1.85 ppm (m, 4H), 1.89 ppm (s, 6H), 2.35 to 2.45 ppm (m, 2H), 2.50 ppm (s, 3H), 2.52 ppm (s, 3H), 2.65 to 2.75 ppm (m, 2H), 4.15 to 4.25 ppm (m, 8H), 5.55 ppm (s, 2H), 6.05 ppm (s, 2H), 7.55 to 7.65 ppm (m, 3H), 7.88 ppm (s, 1H), 7.92 ppm (s, 1H), 8.20 ppm (d, 2H)

A wavelength λmax of the maximum peak of the compound (A4-1) on the longest wavelength side in a range of 300 to 400 nm, which was measured in the same manner as that of the compound (A1-1), was 369 nm.

Synthesis Example 2-5: Synthesis of Compound (A5-1)

(A5-1)

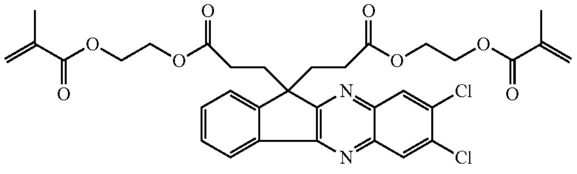

5.1 g of the compound (A5-1) (yield: 84%) was obtained in the same manner as in Synthesis Example 2-1, except that the compound (A1) was changed to the compound (A5).

$^1$H-NMR of compound (A5-1) (400 MHz, $CDCl_3$): δ=1.65 to 1.85 ppm (m, 4H), 1.89 ppm (s, 6H), 2.35 to 2.45 ppm (m, 2H), 2.65 to 2.75 ppm (m, 2H), 4.15 to 4.25 ppm (m, 8H), 5.55 ppm (s, 2H), 6.05 ppm (s, 2H), 7.55 to 7.65 ppm (m, 3H), 8.16 ppm (d, 1H), 8.24 ppm (s, 1H), 8.28 ppm (s, 1H)

A wavelength λmax of the maximum peak of the compound (A5-1) on the longest wavelength side in a range of 300 to 400 nm, which was measured in the same manner as that of the compound (A1-1), was 372 nm.

[Synthesis of Comparative Compound (CA-3)]

[Synthesis of Intermediate 4]

An intermediate 4 was synthesized according to the description in paragraph 0133 of WO2017/115649A.

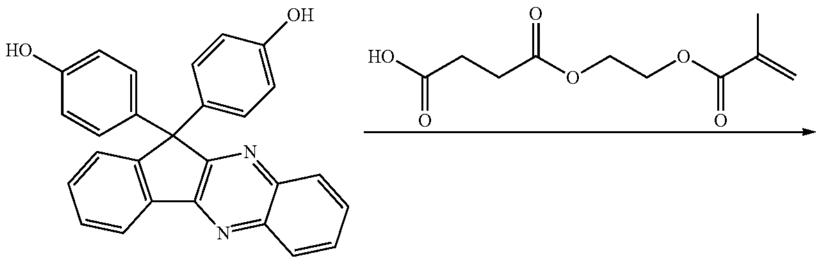

Intermediate 4

-continued

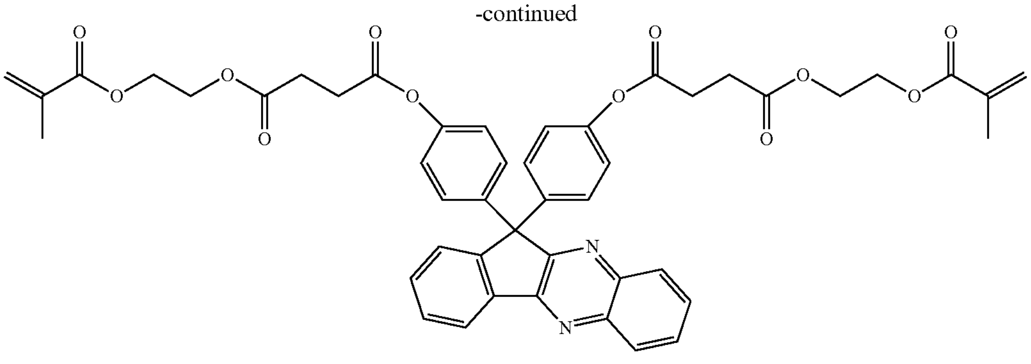

Comparative compound (CA-3)

Into a 200 mL three-neck flask, 4.8 g of the intermediate 4, 6.5 g of mono(2-methacryloyloxyethyl) succinate, 140 mg of N,N-dimethylaminopyridine (DMAP), and 50 mL of dichloromethane were charged, and the mixture was stirred in an ice bath for 10 minutes. 5.8 g of 1-(3-dimethylaminopropyl)-3-ethylcarbodiimide hydrochloride (EDAC HCl) was added thereto, and the mixture was reacted at room temperature for 4 hours. The reaction solution was diluted with ethyl acetate, and washed with water, saturated sodium hydrogen carbonate aqueous solution, and saturated saline in this order, and the organic layer was dried with magnesium sulfate. After removing the magnesium sulfate by filtration, the obtained product was purified by silica gel column chromatography using ethyl acetate/hexane as a developing solvent to obtain 7.5 g of a comparative compound (CA-3).

A wavelength λmax of the maximum peak of the comparative compound (CA-3) on the longest wavelength side in a range of 300 to 400 nm, which was measured in the same manner as that of the compound (A1-1), was 367 nm.

[Synthesis of Comparative Compound (CA-4)]

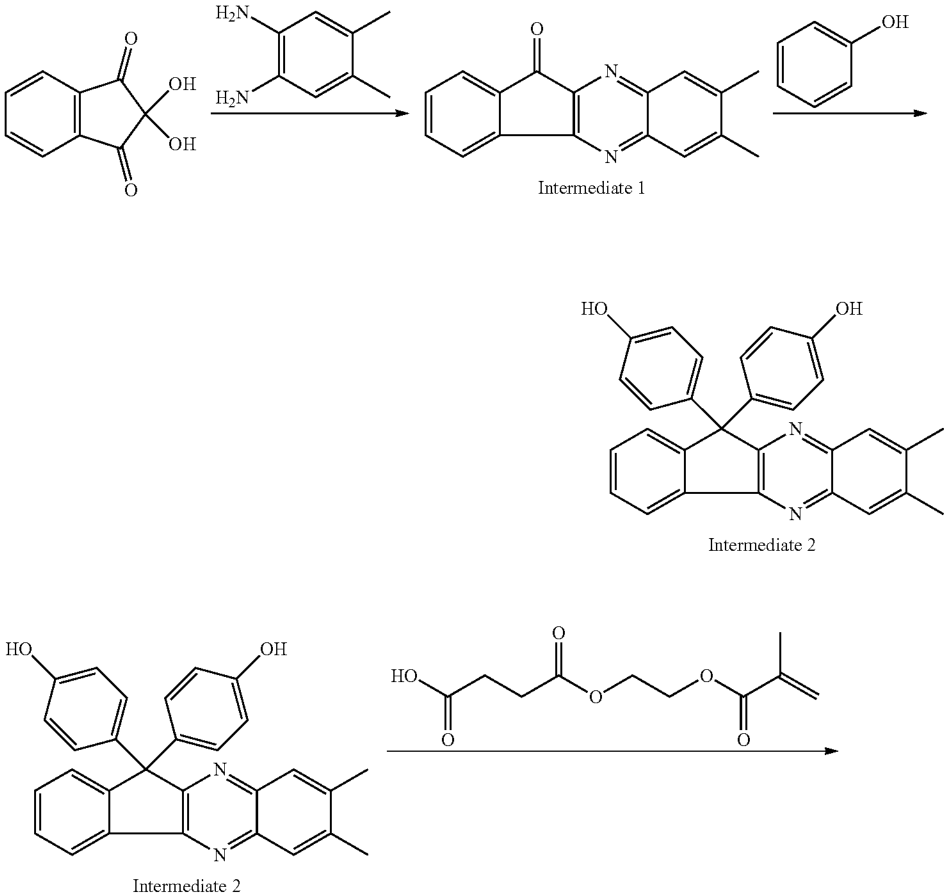

-continued

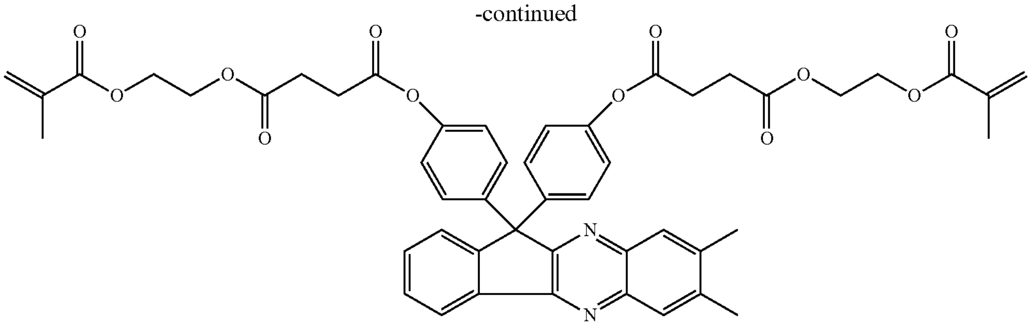

Comparative compound (CA-4)

[Synthesis of Intermediate 1]

50 mL of ethanol and 10 mL of acetic acid were added to 25.6 g of 4,5-dimethyl-1,2-phenylenediamine and 35.6 g of ninhydrin, and the mixture was reacted at 70° C. for 3 hours. The reaction solution was cooled to room temperature, and the precipitated crystals were collected by filtration, washed with ethanol, and dried to obtain 41.1 g of an intermediate 1.

[Synthesis of Intermediate 2]

22 g of the intermediate 1 and 32 g of phenol were dissolved in 20 mL of methanesulfonic acid and 20 mL of acetonitrile. The reaction solution was heated, and 0.3 mL of 3-mercaptopropionic acid was added dropwise thereto while maintaining the temperature at 90° C. After stirring for 3 hours, 200 mL of acetonitrile and 100 mL of water were added thereto, and the reaction solution was stirred in an ice bath for 2 hours. The precipitated crystals were collected by filtration, washed with methanol, and dried to obtain 26 g of an intermediate 2.

[Synthesis of Comparative Compound (CA-4)]

A comparative compound (CA-4) was obtained in the same manner as in the above-described synthesis of the comparative compound (CA-3), except that the intermediate 4 was changed to the intermediate 2.

A wavelength λmax of the maximum peak of the comparative compound (CA-4) on the longest wavelength side in a range of 300 to 400 nm, which was measured in the same manner as that of the compound (A1-1), was 374 nm.

[Synthesis of Comparative Compound (CA-5)]

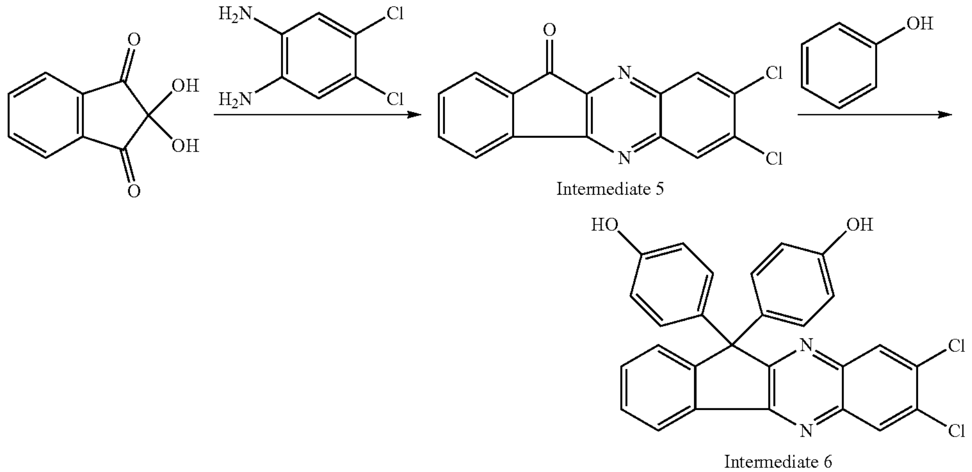

Intermediate 5

Intermediate 6

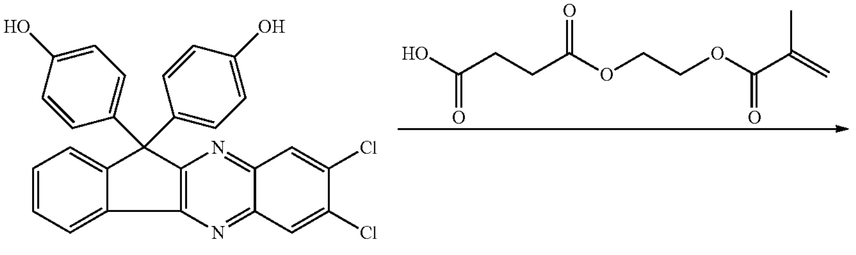

Intermediate 6

-continued

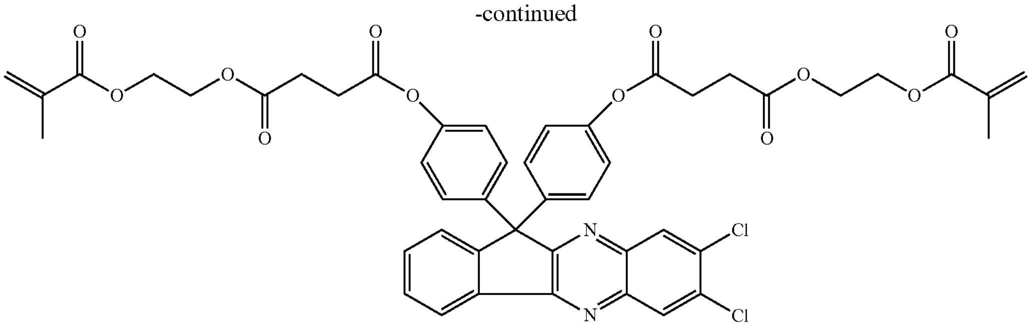

Comparative compound (CA-5)

[Synthesis of Intermediate 5]

An intermediate 5 was obtained in the same manner as in the above-described synthesis of the intermediate 1, except that 4,5-dimethyl-1,2-phenylenediamine was changed to 4,5-dichloro-1,2-phenylenediamine.

[Synthesis of Intermediate 6]

An intermediate 6 was obtained in the same manner as in the above-described synthesis of the intermediate 2, except that the intermediate 1 was changed to the intermediate 5.

[Synthesis of Comparative Compound (CA-5)]

A comparative compound (CA-5) was obtained in the same manner as in the above-described synthesis of the comparative compound (CA-3), except that the intermediate 4 was changed to the intermediate 6.

A wavelength λmax of the maximum peak of the comparative compound (CA-5) on the longest wavelength side in a range of 300 to 400 nm, which was measured in the same manner as that of the compound (A1-1), was 377 nm.

[3. Synthesis of Polymer Having Radically Polymerizable Group in Side Chain]

A polymer (G-1) having a radically polymerizable group in the side chain was synthesized by the following method.

12.0 g of benzyl methacrylate and 18.0 g of allyl methacrylate were dissolved in 172.3 g of methyl ethyl ketone, and the mixture was heated to 70° C. The solution was added dropwise over 30 minutes to a solution in which 1.05 g of a polymerization initiator V-65 (product name, manufactured by FUJIFILM Wako Pure Chemical Corporation, oil-soluble azo polymerization initiator) was dissolved in 12.0 g of methyl ethyl ketone. After the completion of the dropwise addition, the reaction was further performed at 70° C. for 4.5 hours. The reaction solution was allowed to cool and concentrated until the total amount thereof reached 107.7 g, and then 42.0 g of methanol was added thereto and stirred until the reaction solution was homogeneous. The reaction solution was added dropwise to 858.0 g of methanol cooled to 5° C. or lower, and the precipitated powder was collected by filtration and dried. In this way, 20.5 g of the polymer (G-1) was obtained. The weight-average molecular weight of the obtained polymer was 35700, and the dispersibility (Mw/Mn) was 3.3.

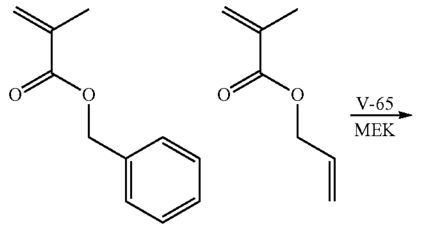

-continued

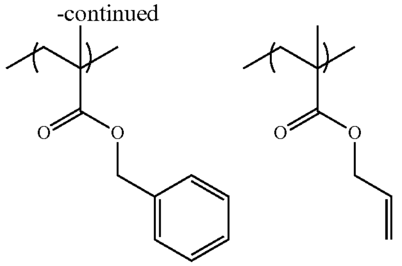

G-1

The weight-average molecular weight and the dispersibility of the polymer produced above are a weight-average molecular weight and a dispersibility in terms of standard polystyrene by gel permeation chromatography (GPC), and are values measured under the following conditions.

Measuring instrument: HLC-8320GPC (product name, manufactured by Tosoh Corporation)

Column: connection of TOSOH TSKgel HZM-H (product name, manufactured by Tosoh Corporation), TOSOH TSKgel HZ4000 (product name, manufactured by Tosoh Corporation), and TOSOH TSKgel HZ2000 (product name, manufactured by Tosoh Corporation)

Carrier: THF

Measurement temperature: 40° C.

Carrier flow rate: 0.35 ml/min

Sample concentration: 0.1% by mass

Detector: refractive index (RI) detector

Example 1: Preparation of Curable Resin Composition

The compound represented by General Formula (A) or (B) or the comparative compound, other monomers, a photopolymerization initiator, a thermal polymerization initiator, and other additives were mixed and stirred to be homogeneous, a curable resin composition was prepared so as to have a composition shown in Table 1 below.

Curable resin compositions Nos. 101 to 115 are Examples, and curable resin compositions Nos. c11 to c16 are Comparative Examples.

[Evaluation 1] Measurement of Viscosity of Curable Resin Composition

A viscosity of the produced curable resin composition was measured using a reometer (product name: RS600) manufactured by HAAKE under the conditions of 25° C. and a shear rate of 10 $s^{-1}$. The results are summarized in Table 1.

Example 2: Production of Cured Product

The obtained curable resin composition was injected into a circular transparent glass mold having a diameter of 20 mm so that a thickness of a cured product was 1 mm. The glass mold is made of borosilicate glass in which a surface is hydrophobically treated with dichlorodimethylsilane.

Using Execure 3000 (product name, manufactured by HOYA CORPORATION) as a light source, a photocured sample was produced by irradiating ultraviolet rays of 1000 mJ/$cm^2$ from above the transparent glass mold in a nitrogen-substituted atmosphere so that an oxygen concentration was 1% or less. Subsequently, the obtained photocured sample was heated at 200° C. for 30 minutes in an atmosphere having an oxygen concentration of 1% or less to produce a cured product in which the curing reaction completely proceeded.

[Evaluation 2] Evaluation of Refractive Index of Cured Product

A refractive index nD of the obtained cured product at a wavelength of 589 nm was measured under a condition of 25° C. using an Abbe refractionometer (manufactured by ATAGO CO., LTD., product name: DR-M4). In addition, nF, nC, and ng were also measured, and as wavelength dispersion characteristics of the refractive index, the Abbe number νD and the partial dispersion ratio θg, F were obtained from the following expressions. The results are summarized in Table 1.

$$\nu D=(nD-1)/(nF-nC)$$

$$\theta g,F=(ng-nF)/(nF-nC)$$

Here, nF represents a refractive index at a wavelength of 486 nm, nC represents a refractive index at a wavelength of 656 nm, and ng represents a refractive index at a wavelength of 436 nm.

[Evaluation 3] Evaluation of Transmittance of Cured Product

With regard to the obtained cured product, using an ultraviolet-visible spectrophotometer UV-2600 (product name, manufactured by Shimadzu Corporation), an ultraviolet-visible transmittance measurement was performed on a central portion (5 mm in diameter) to measure a transmittance at a wavelength of 420 nm. The results are summarized in Table 1. In addition, the FIGURE shows a graph showing a relationship between the Abbe number νD and the transmittance.

[Evaluation 4] Birefringence Index Δn

Using a birefringence evaluation device (WPA-100 (product name), manufactured by Photonic Lattice, Inc.), a birefringence within a circle having a diameter of 10 mm including the center of the cured product (cured product sample for optical measurement) produced above at a wavelength of 543 nm was measured, and the average value thereof was defined as a birefringence index Δn.

All of cured products obtained from the curable resin compositions Nos. 101 to 115 had a small birefringence Δn of 0.0003 to 0.0009, and could obtain a clear image without shifting an imaging position, so that the cured product was suitable for use as an optical member of an imaging module.

TABLE 1

| | | Curable resin composition | 101 | 102 | 103 | 104 | 105 |
|---|---|---|---|---|---|---|---|
| Composition | Composed represented by General Formula (A) or (B) | A1-1 | 80 | 85 | — | — | — |
| | | A2-1 | — | — | 80 | 85 | — |
| | | A3-1 | — | — | — | — | 45 |
| | | A4-1 | — | — | — | — | — |
| | | A5-1 | — | — | — | — | — |
| | Other monomers | PEA | 19.8 | 14.8 | 19.8 | 14.8 | 19.8 |
| | | OPPE | — | — | — | — | 25 |
| | | BzMA | — | — | — | — | — |
| | | HDDMA | — | — | — | — | — |
| | Photopolymerization initiator | Irg819 | — | — | — | — | 0.1 |
| | | IrgTPO | 0.1 | 0.1 | 0.1 | 0.1 | — |
| | Thermal polymerization initiator | PERHEXYL D | 0.1 | 0.1 | 0.1 | 0.1 | 0.1 |
| | Other additives | G-1 | — | — | — | — | 10 |
| | Total | | 100 | 100 | 100 | 100 | 100 |
| Evaluation | Viscosity of curable resin composition (cP) | | 5400 | 14500 | 6200 | 17900 | 1800 |
| | Refractive index characteristics of cured product | nD | 1.619 | 1.622 | 1.609 | 1.611 | 1.586 |
| | | νD | 21.2 | 20.8 | 20.1 | 19.5 | 22.8 |
| | | θg, F | 0.67 | 0.67 | 0.72 | 0.72 | 0.73 |
| | Transmittance of cured product | | 85.0% | 84.1% | 82.7% | 81.4% | 76.8% |

| | | Curable resin composition | 106 | 107 | 108 | 109 | 110 |
|---|---|---|---|---|---|---|---|
| Composition | Composed represented by General Formula (A) or (B) | A1-1 | — | — | — | — | — |
| | | A2-1 | — | — | — | — | — |
| | | A3-1 | 55 | 65 | 75 | 80 | 85 |
| | | A4-1 | — | — | — | — | — |
| | | A5-1 | — | — | — | — | — |
| | Other monomers | PEA | 19.8 | 19.8 | 19.8 | 19.8 | 14.8 |
| | | OPPE | 15 | 10 | — | — | — |
| | | BzMA | — | — | — | — | — |
| | | HDDMA | — | — | 5 | — | — |

TABLE 1-continued

| | | | | | | | |
|---|---|---|---|---|---|---|---|
| | Photopolymerization initiator | Irg819 | 0.1 | 0.1 | 0.1 | 0.1 | 0.1 |
| | | IrgTPO | — | — | — | — | — |
| | Thermal polymerization initiator | PERHEXYL D | 0.1 | 0.1 | 0.1 | 0.1 | 0.1 |
| | Other additives | G-1 | 10 | 5 | — | — | — |
| | Total | | 100 | 100 | 100 | 100 | 100 |
| Evaluation | Viscosity of curable resin composition (cP) | | 2400 | 2200 | 1900 | 4100 | 9600 |
| | Refractive index characteristics of cured product | nD | 1.591 | 1.596 | 1.599 | 1.601 | 1.604 |
| | | vD | 22.0 | 21.3 | 20.6 | 20.1 | 19.6 |
| | | θg, F | 0.76 | 0.78 | 0.79 | 0.81 | 0.83 |
| | Transmittance of cured product | | 75.9% | 74.3% | 72.6% | 71.7% | 70.5% |

| | | Curable resin composition | 111 | 112 | 113 | 114 | 115 |
|---|---|---|---|---|---|---|---|
| Composition | Composed represented by General Formula (A) or (B) | A1-1 | — | — | — | — | — |
| | | A2-1 | — | — | — | — | — |
| | | A3-1 | — | — | — | — | — |
| | | A4-1 | 80 | 85 | — | — | — |
| | | A5-1 | — | — | 80 | 85 | 85 |
| | Other monomers | PEA | 19.8 | 14.8 | 19.8 | 14.8 | — |
| | | OPPE | — | — | — | — | — |
| | | BzMA | — | — | — | — | 14.8 |
| | | HDDMA | — | — | — | — | — |
| | Photopolymerization initiator | Irg819 | 0.1 | 0.1 | 0.1 | 0.1 | 0.1 |
| | | IrgTPO | — | — | — | — | — |
| | Thermal polymerization initiator | PERHEXYL D | 0.1 | 0.1 | 0.1 | 0.1 | 0.1 |
| | Other additives | G-1 | — | — | — | — | — |
| | Total | | 100 | 100 | 100 | 100 | 100 |
| Evaluation | Viscosity of curable resin composition (cP) | | 3200 | 7200 | 4600 | 12000 | 11600 |
| | Refractive index characteristics of cured product | nD | 1.600 | 1.603 | 1.610 | 1.613 | 1.614 |
| | | vD | 18.5 | 18.0 | 17.9 | 17.4 | 17.4 |
| | | θg, F | 0.85 | 0.87 | 0.89 | 0.92 | 0.91 |
| | Transmittance of cured product | | 73.1% | 72.8% | 67.3% | 66.1% | 66.6% |

| | | Curable resin composition | c11 | c12 | c13 | c14 | c15 | c16 |
|---|---|---|---|---|---|---|---|---|
| Composition | Comparative compound | CA-1 | 80 | — | — | — | — | — |
| | | CA-2 | — | 80 | — | — | — | — |
| | | CA-3 | — | — | 80 | — | — | — |
| | | CA-4 | — | — | — | 80 | — | — |
| | | CA-5 | — | — | — | — | 80 | — |
| | | CA-6 | — | — | — | — | — | 80 |
| | Other monomers | PEA | 19.8 | 19.8 | 19.8 | 19.8 | 19.8 | 19.8 |
| | | OPPE | — | — | — | — | — | — |
| | | BzMA | — | — | — | — | — | — |
| | | HDDMA | — | — | — | — | — | — |
| | Photopolymerization initiator | Irg819 | — | — | 0.1 | 0.1 | 0.1 | 0.1 |
| | | IrgTPO | 0.1 | 0.1 | — | — | — | — |
| | Thermal polymerization initiator | PERHEXYL D | 0.1 | 0.1 | 0.1 | 0.1 | 0.1 | 0.1 |
| | Other additives | G-1 | — | — | — | — | — | — |
| | Total | | 100 | 100 | 100 | 100 | 100 | 100 |
| Evaluation | Viscosity of curable resin composition (cP) | | 86000 | 195000 | 77000 | 59000 | 86000 | 135000 |
| | Refractive index characteristics of cured product | nD | 1.638 | 1.629 | 1.606 | 1.599 | 1.600 | 1.630 |
| | | vD | 21.8 | 20.4 | 21.1 | 20.4 | 20.2 | 20.9 |
| | | θg, F | 0.67 | 0.72 | 0.79 | 0.81 | 0.83 | 0.80 |
| | Transmittance of cured product | | 79.6% | 76.7% | 65.1% | 62.0% | 59.1% | 59.0% |

<Note to table>

Each component in the tables is as follows. The blending amount ratio of each component described in the column of each component is based on mass, and "—" indicates that the component is not contained.

(Compound Represented by General Formula (A) or (B))

(A1-1)

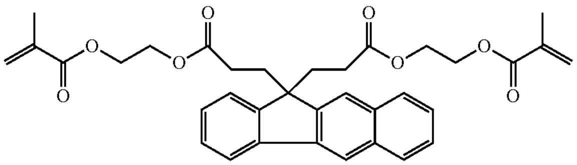

-continued (A2-1)

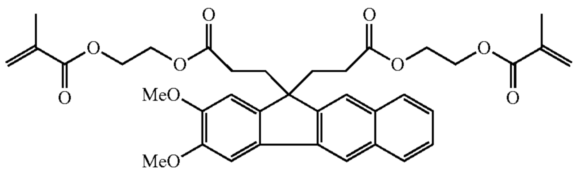

-continued
(A3-1)
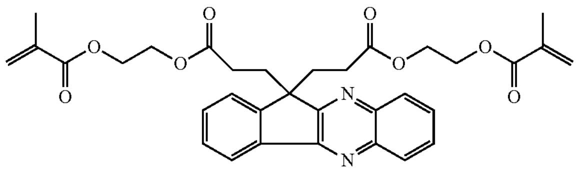
(A4-1)
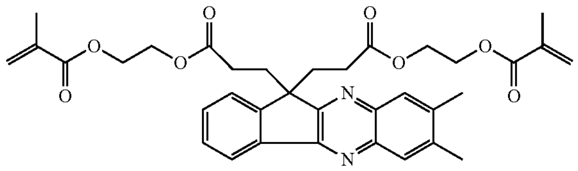
-continued
(A5-1)
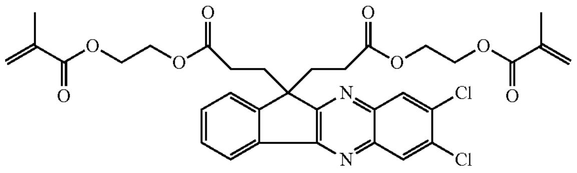
(Comparative Compound)
Comparative compound (CA-1)
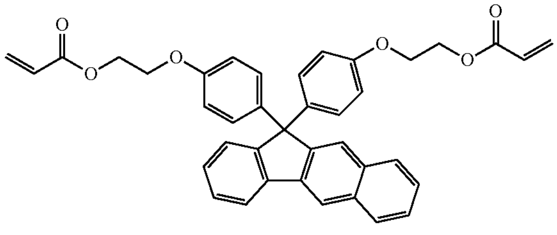
Comparative compound (CA-2)
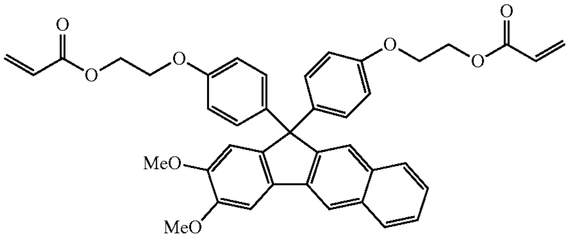
Comparative compound (CA-3)
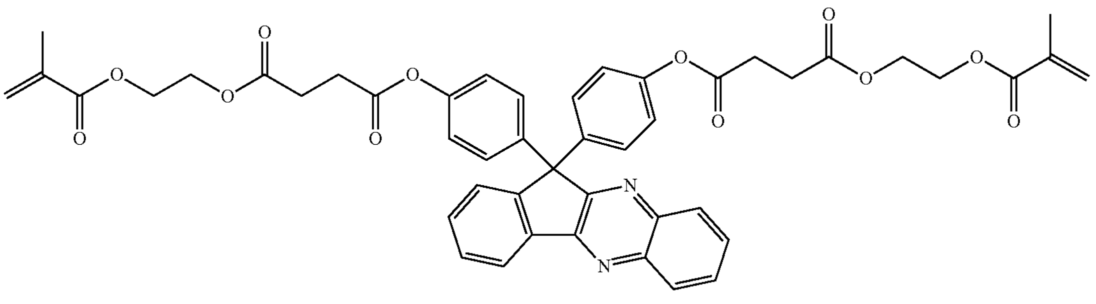
Comparative compound (CA-4)
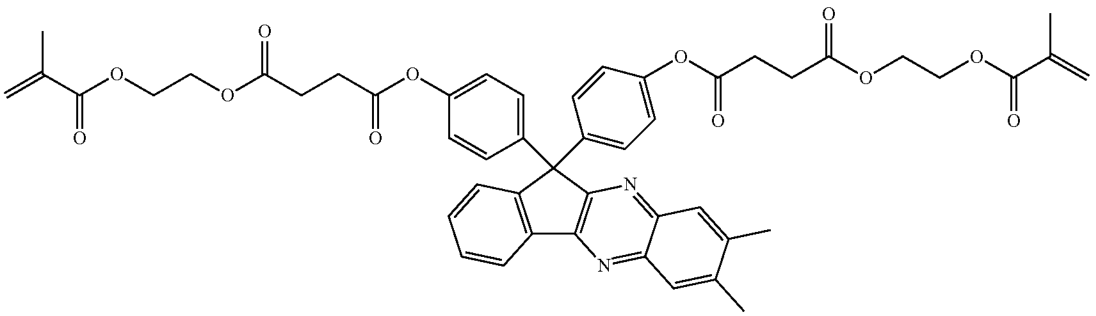

-continued

Comparative compound (CA-5)

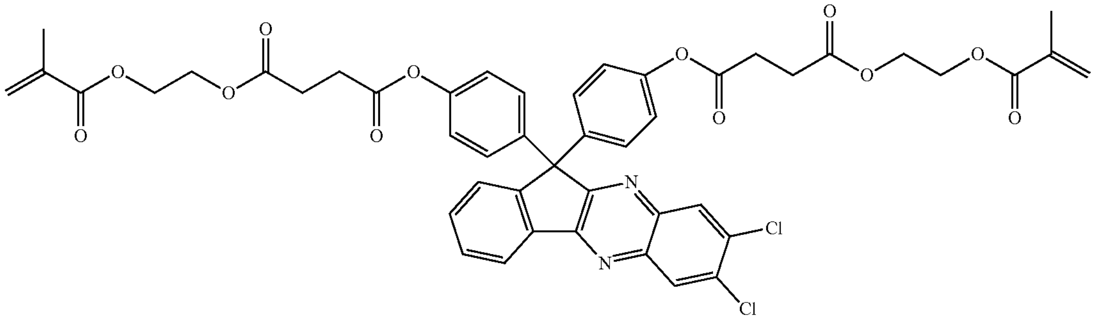

Comparative compound (CA-6)

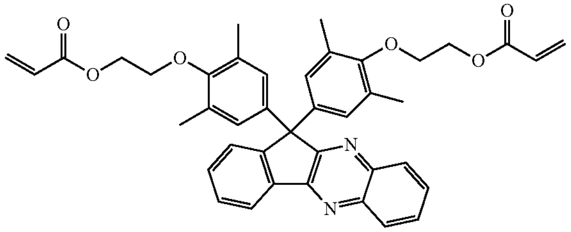

The comparative compound (CA-1) was synthesized according to the synthesis method described in Example 1 of JP2014-80572A.

The comparative compound (CA-2) was synthesized according to <Synthesis of compound 2-1> of WO2016/140245A.

The comparative compound (CA-6) was synthesized according to the synthesis of the compound (51) of WO2017/115649A (JP6606195B).

In a case where, similarly to the compound (A1-1), the wavelengths λmax of the maximal peaks of the comparative compounds (CA-1), (CA-2), and (CA-6) on the longest wavelength side in a range of 300 to 400 nm were measured, the comparative compound (CA-1) was 347 nm, the comparative compound (CA-2) was 359 nm, and the comparative compound (CA-6) was 368 nm.

(Other Monomers)

The compounds represented below are shown respectively.

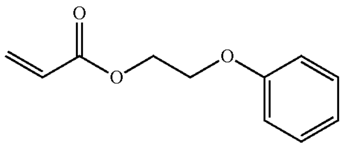

PEA

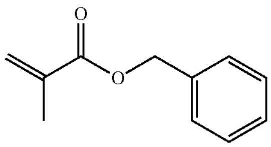

BzMA

-continued

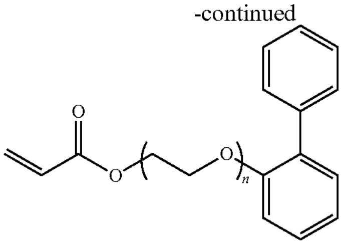

n = 1 - 2

OPPE

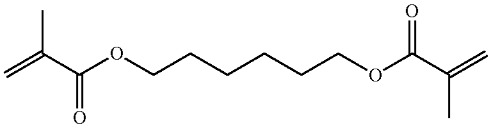

HDDMA (Photopolymerization Initiator)

Irg819: Irgacure 819 (product name, manufactured by BASF SE)

IrgTPO: Irgacure TPO (product name, manufactured by BASF SE)

(Thermal polymerization initiator)

PERHEXYL D: product name, manufactured by NOF CORPORATION, di-tert-hexyl peroxide (Other Additives)

G-1: polymer (G-1) produced above

G-1

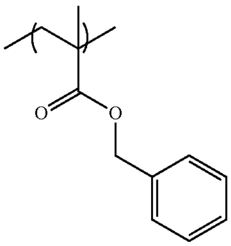

-continued

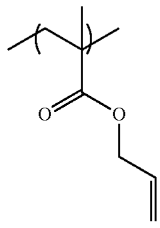

From the results shown in Table 1 and the FIGURE, the following is found.

The comparative compound (CA-1) is not the compound according to the embodiment of the present invention in that it has a phenylene group as $L^1$ and $L^2$ in General Formula (A). In the cured product obtained from the curable resin composition No. c11 containing the comparative compound (CA-1), the Abbe number νD was 21.8 and the transmittance was 79.6%. On the other hand, in the compound (A1-1) according to the embodiment of the present invention, $L^1$ and $L^2$ in General Formula (A) are alkylene groups, and the fused-ring structure to which $L^1$ and $L^2$ are bonded is the same as that of the comparative compound (CA-1). In the cured product obtained from the curable resin composition No. 101 which contained the compound (A1-1) according to the embodiment of the present invention in the same amount as the comparative compound (CA-1), although the Abbe number νD was 21.2, which was lower than that of the comparative compound (CA-1), the transmittance was 85.0%, which was significantly higher than that of the comparative compound (CA-1).

The comparative compound (CA-2) is not the compound according to the embodiment of the present invention in that it has a phenylene group as $L^1$ and $L^2$ in General Formula (A). In the cured product obtained from the curable resin composition No. c12 containing the comparative compound (CA-2), the Abbe number νD was 20.4 and the transmittance was 76.7%. On the other hand, in the compound (A2-1) according to the embodiment of the present invention, $L^1$ and $L^2$ in General Formula (A) are alkylene groups, and the fused-ring structure to which $L^1$ and $L^2$ are bonded is the same as that of the comparative compound (CA-2). In the cured product obtained from the curable resin composition No. 103 which contained the compound (A2-1) according to the embodiment of the present invention in the same amount as the comparative compound (CA-2), although the Abbe number νD was 20.1, which was lower than that of the comparative compound (CA-2), the transmittance was 82.7%, which was significantly higher than that of the comparative compound (CA-2).

The comparative compound (CA-3) is not the compound according to the embodiment of the present invention in that it has a phenylene group as $L^1$ and $L^2$ in General Formula (A). In the cured product obtained from the curable resin composition No. c13 containing the comparative compound (CA-3), the Abbe number νD was 21.1 and the transmittance was 65.1%. In addition, the comparative compound (CA-6) is not the compound according to the embodiment of the present invention in that it has a dimethylphenylene group as $L^1$ and $L^2$ in General Formula (A). In the cured product obtained from the curable resin composition No. c16 containing the comparative compound (CA-6), the Abbe number νD was 20.9 and the transmittance was 59.0%. On the other hand, in the compound (A3-1) according to the embodiment of the present invention, $L^1$ and $L^2$ in General Formula (A) are alkylene groups, and the fused-ring structure to which $L^1$ and $L^2$ are bonded is the same as that of the comparative compounds (CA-3) and (CA-6). In the cured product obtained from the curable resin composition No. 109 which contained the compound (A3-1) according to the embodiment of the present invention in the same amount as the comparative compounds (CA-3) and (CA-6), although the Abbe number νD was 20.1, which was lower than that of the comparative compounds (CA-3) and (CA-6), the transmittance was 71.7%, which was outstandingly higher than that of the comparative compounds (CA-3) and (CA-6).

The comparative compound (CA-4) is not the compound according to the embodiment of the present invention in that it has a phenylene group as $L^1$ and $L^2$ in General Formula (A). In the cured product obtained from the curable resin composition No. c14 containing the comparative compound (CA-4), the Abbe number νD was 20.4 and the transmittance was 62.0%. On the other hand, in the compound (A4-1) according to the embodiment of the present invention, $L^1$ and $L^2$ in General Formula (A) are alkylene groups, and the fused-ring structure to which $L^1$ and $L^2$ are bonded is the same as that of the comparative compound (CA-4). In the cured product obtained from the curable resin composition No. 111 which contained the compound (A4-1) according to the embodiment of the present invention in the same amount as the comparative compound (CA-4), although the Abbe number νD was 18.5, which was outstandingly lower than that of the comparative compound (CA-4), the transmittance was 73.1%, which was significantly higher than that of the comparative compound (CA-4).

The comparative compound (CA-5) is not the compound according to the embodiment of the present invention in that it has a phenylene group as $L^1$ and $L^2$ in General Formula (A). In the cured product obtained from the curable resin composition No. c15 containing the comparative compound (CA-5), the Abbe number νD was 20.2 and the transmittance was 59.1%. On the other hand, in the compound (A5-1) according to the embodiment of the present invention, $L^1$ and $L^2$ in General Formula (A) are alkylene groups, and the fused-ring structure to which $L^1$ and $L^2$ are bonded is the same as that of the comparative compound (CA-5). In the cured product obtained from the curable resin composition No. 113 which contained the compound (A5-1) according to the embodiment of the present invention in the same amount as the comparative compound (CA-5), although the Abbe number νD was 17.9, which was outstandingly lower than that of the comparative compound (CA-5), the transmittance was 67.3%, which was significantly higher than that of the comparative compound (CA-5).

From these results, it was found that, by using the compound according to the embodiment of the present invention, it was possible to obtain a cured product in which both a low Abbe number and a high transmittance were achieved at a high level compared to the compound in the related art, in which $L^1$ and $L^2$ bonded to the fused-ring structure were phenylene groups or dimethylphenylene groups. Among these, the compound (A2-1) according to the embodiment of the present invention was excellent in achieving both the low Abbe number and the high transmittance. In addition, the compound (A5-1) according to the embodiment of the present invention was excellent in that it exhibited a higher partial dispersion ratio θg, F, in addition to achieving both the low Abbe number and the high transmittance at a high level.

From the comparison between No. 101 and No. 102, comparison between No. 103 and No. 104, comparison between Nos. 105 to 110, comparison between No. 111 and No. 112, and comparison between No. 113 and No. 114, in which the contents of the compounds (A1-1) to (A5-1) according to the embodiment of the present invention in the curable resin composition varied, it was found that, in a case where the same compound was used, there is a trade-off relationship between the Abbe number νD and the transmittance depending on the content. That is, in this respect, the results as previously found were obtained.

In addition, in addition to the low Abbe number νD and the high transmittance described above, the cured product obtained from the curable resin composition containing the compound according to the embodiment of the present invention had a sufficiently high partial dispersion ratio θg, F of 0.67 or more, and was excellent in refractive index wavelength dispersion characteristics in a case of being used as a chromatic aberration correction lens.

The present invention has been described with the embodiments thereof, any details of the description of the present invention are not limited unless described otherwise, and it is obvious that the present invention is widely construed without departing from the gist and scope of the present invention described in the accompanying claims.

What is claimed is:

1. A compound represented by General Formula (A1) or (B),

General Formula (A1)

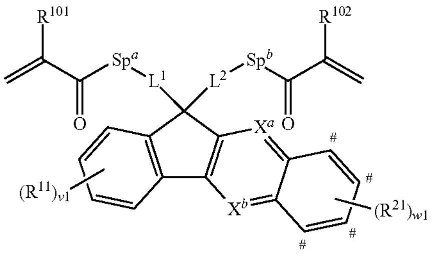

in the formulae, $X^a$ and $X^b$ represent a nitrogen atom or CH,

CH at a position of # may be substituted by a nitrogen atom, $R^{11}$ and $R^{21}$ represent a substituent, v1 and w1 are an integer of 0 to 4, $R^{101}$ and $R^{102}$ represent a hydrogen atom or a methyl group, $L^1$ and $L^2$ represent an alkylene group having 1 to 6 carbon atoms, and $Sp^a$ to $Sp^d$ represent a single bond or a divalent linking group.

2. A curable resin composition comprising:

the compound according to claim 1 represented by General Formula (A1).

3. The curable resin composition according to claim 2, wherein a content of the compound represented by General Formula (A1) in the curable resin composition is 50% by mass or more.

4. A cured product of the curable resin composition according to claim 2.

5. An optical member comprising:

the cured product according to claim 4.

6. A lens comprising:

the cured product according to claim 4.

* * * * *